US008143307B2

(12) United States Patent
Yi et al.

(10) Patent No.: US 8,143,307 B2
(45) Date of Patent: Mar. 27, 2012

(54) BENZOTHIOPHEN-2-CARBONYL-GUANIDINE DERIVATIVES, PREPARATION THEREOF, AND PHARMACEUTICAL COMPOSITION CONTAINING THE SAME

(75) Inventors: Kyu Yang Yi, Taejeon-si (KR); SunKyung Lee, Taejeon-si (KR); Jee Hee Suh, Taejeon-si (KR); Nak Jeong Kim, Taejeon-si (KR); Hyunsuk Lee, Chungcheongnam-do (KR); Byung-Ho Lee, Taejeon-si (KR); Sung-eun Yoo, Kongju-si (KR); Kyung-Hee Lee, Sungnam-si (KR); Yong Oh Lee, Koyang-si (KR)

(73) Assignee: Korea Research Institute of Chemical Technology, Taejeon-si (KR)

( * ) Notice: Subject to any disclaimer, the term of this patent is extended or adjusted under 35 U.S.C. 154(b) by 639 days.

(21) Appl. No.: 11/794,238

(22) PCT Filed: Dec. 27, 2005

(86) PCT No.: PCT/KR2005/004573
§ 371 (c)(1),
(2), (4) Date: Sep. 9, 2009

(87) PCT Pub. No.: WO2006/071047
PCT Pub. Date: Jul. 6, 2006

(65) Prior Publication Data
US 2010/0004466 A1    Jan. 7, 2010

(30) Foreign Application Priority Data

Dec. 27, 2004 (KR) .................... 10-2004-0112856

(51) Int. Cl.
*A61K 31/381* (2006.01)
*C07D 333/56* (2006.01)
(52) U.S. Cl. .......................... 514/443; 549/57
(58) Field of Classification Search ................ 514/443; 549/57
See application file for complete search history.

(56) References Cited

U.S. PATENT DOCUMENTS 5,753,680 A    5/1998  Gericke et al.
6,627,643 B2   9/2003  Busch et al.

FOREIGN PATENT DOCUMENTS

JP    09-278767    10/1997
JP    10-316647    12/1998

OTHER PUBLICATIONS

Benos, Dale J.; "Amiloride: a molecular proble of sodium transport in tissues and cells", *the American Physiological Society*, 242, 1982, pp. C131-C145.
Scholz, W. et al.: "Hoe 694, a new $Na^+/H^+$ exchange inhibitor and its effect in cardiac ischaemia", *Br. J. Pharmacol.*, (1933, 109, p. 562-568.
Karmazyn, Morris; "Sodium-Hydrogen Exchange in Heart Disease", *Science & Medicine*, Jan./Feb. 2002, pp. 18-27.
Avkiran, Metin et al.; "$Na^+/H^+$ Exchange Inhibitors for Cardioprotective Therapy: Progress, Problems and Prospects", *Journal of the American College of Cardiology*, vol. 39, No. 5, 2002, pp. 747-753.
Kloner, Robert A. et al.: "Cardiac Protection During Acute Myocardial Infarction: Where Do We Stand in 2004?", *Journal of the American College of Cardiology*, vol. 44, No. 2, 2004, pp. 276-286.
Mentzer, Robert M. Jr. et al.: "Intracellular Sodium Hydrogen Exchange Inhibition and Clinical Myocardial Protection", *Ann. Thorac. Surg.*, 2003, 75, pp. 5700-5708.

*Primary Examiner* — Taofiq A Solola
(74) *Attorney, Agent, or Firm* — Frommer Lawrence & Haug LLP; Ronald R Santucci

(57) ABSTRACT

The present invention is related to benzothiophen-2-carbonylguanidine derivatives, a preparation method thereof, and pharmaceutical compositions containing the same. The derivatives have potent inhibitory effect on the sodium/hydrogen exchanger NHE-I, improve the functional recovery of ischemia/reperfusion-induced heart injury in isolated ischemic heart models, and significantly reduce the myocardiac infarct size in in vivo ischemic animal models, thereby showing excellent cardioprotective effects. Also, the derivatives are protective of both neuronal cells and the brain as proven by their protective effects on neuronal cells from necrosis and apoptosis and by their ability to significantly reduce cerebral infarct sizes in in vivo ischemic brain models. The derivatives can be effectively used for the prevention and treatment of ischemic heart diseases such as myocardiac infarction, arrhythmia, angina pectoris and the like, and cerebrovascular diseases such as cerebral stroke and be used as cardioprotective agents to the patients undergoing reperfusion therapy including chemicals such as thrombolytic agents, or surgery such as coronary artery bypass and percutaneous transluminal coronary angioplasty.

4 Claims, No Drawings

BENZOTHIOPHEN-2-CARBONYLGUANIDINE DERIVATIVES, PREPARATION THEREOF, AND PHARMACEUTICAL COMPOSITION CONTAINING THE SAME

This application is a 371 of PCT/KR2005/004573 filed on Dec. 27, 2005, published on Jul. 6, 2006 under publication number WO 2006/071047 A1 which claims priority benefits from Korean Patent Application No. 10-2004-0112856 filed Dec. 27, 2004, the disclosure of which is hereby incorporated by reference.

TECHNICAL FIELD

The present invention relates to benzothiophen-2-carbonylguanidine derivatives, preparation thereof, and pharmaceutical compositions containing the same.

BACKGROUND ART

Although coronary reperfusion therapy with chemicals such as thrombolytic agents, or surgery such as coronary artery bypass and percutaneous transluminal coronary angioplasty immediately after ischemic heart diseases such as acute myocardial infarction, arrhythmia, heart failure, etc., increases the survival rate of patients suffering therefrom, the effect thereof remains controversial because of aftereffects including a high recurrence rate of myocardiac infarction or arrhythmia, or cardiac dysfunction or neurocognitive dysfunction [Robert, M. (2003) *Ann. Thorac. Surg.* 75: S700-708]. Thus, there is a need for a heart protection agent that can delay the progress of ischemic damage to cardiomyocytes and protect reperfusion-induced injuries [Kloner, R. A.; Rezkalla, S. H. (2004) *J. Am. Coll. Cardiol.* 44: 276-286].

NHE (sodium-hydrogen exchanger) is an ion channel expressed in various cell species, playing an important role in intracellular pH control. Thus far, 7 subtypes have been found, with NHE-1, major subtype in myocardiac cell, known to play a pivotal role in myocardial ischemic-reperfusional injury [Avkiran, M. et al., (2002) *J. Am. Coll. Cardiol.* 39: 747-753]. NHE-1 doesn't work at a normal physiological pH condition (7.2). NHE-1 is activated by the profound intracellular acidosis (pH=6.4) that accompanies ischemia. The efflux of $H^+$ through the activated NHE-1 is increased, causing intracellular $Na^+$ overload, which leads to intracellular $Ca^{2+}$ overload through a reverse mode of NCX ($Na^+/Ca^{2+}$ exchanger). An increase of intracellular calcium ions activates enzymes, such as proteases, phospholipase, endonucleases, etc., to cause protein degradation, ROS (reactive oxygen species) increase attributed to lipid metabolism hindrance, DNA damage, and finally, cell injury. This leads to the conclusion that the inhibition of NHE-1 reduces intracellular $Na^+$ ion overload and thus intracellular $Ca^{2+}$ ion overload, thereby protecting cells from ischemic/reperfusional injury. However, the inhibition of NHE-1 does not induce the intracellular acidosis as the increased intracellular hydrogen ion concentration is controlled by other ion channels.

The pyrazine derivative amiloride, used as a diuretic agent, was found at first to function as an NHE inhibitor [Benos, D J. (1982) *A. J. Physiol.* 242: C131]. In a rat ischemic heart model, amiloride was observed to improve cardiac function recovery after ischemia/reperfusion by the inhibition of NHE-1. However, amiloride has a problem as a carioprotecting agent due to a lack of selectivity for NHE-1, as it was found to inhibit NHE-2 and sodium channels as well as NHE-1.

Hence, extensive research has been done in order to develop the agents specific for NHE-1, and Hoechst Marion Roussel (now Aventis) succeeded in developing cariporide (HOE-694), a benzoyl guanidine derivative highly specific for NHE-1 [Scholz, W. et. al., (1993) *Br. J. Pharmacol.* 109: 562]. Almost all of the NHE-1 inhibitors known so far are acylguanidines, as exemplified by the selective NHE-1 inhibitors zoniporide, sabiporide, SM-20220, BMS-284640, etc.

It was found that the protective effects of NHE-1 inhibitors on ischemic reperfused hearts, that is, apoptosis or necrosis reduction, functional recovery of injured myqcardium, arrhythmia reduction, and metabolic status improvement, can be achieved by reducing the intracellular overload of sodium and calcium ions [Karmazyn, M. (2002) *Science & Medicine*: 18-26]. Hence, functioning as cardioprotectives against ischemia/reperfusion injury, selective NHE-1 inhibitors can be applied to the patients undergoing reperfusion therapy including coronary artery bypass, percutaneous transluminal coronary angioplasty and/or thrombolytics for acute myocardiac infarction, and therefore will live up to the hope of treatment and prevention of a broad spectrum of ischemic heart diseases including heart failure, arrhythmia, etc.

Leading to the present invention, the intensive and thorough research on selective NHE-1 inhibitors, conducted by the present inventors, resulted in the finding that benzothiophen-2-carbonylguanidine derivatives as selective inhibitors of NHE-1, are effective in functional recovery of ischemia/reperfusion-induced myocardial injury, and neuroprotective against apoptosis, in addition to having a significant reduction in infarction size as measured in cerebral and cardiac ischemia models, thereby greatly contributing to the treatment and prevention of ischemic heart and brain diseases.

DISCLOSURE

Technical Problem

Therefore, it is an object of the present invention to provide benzothiophen-2-carbonylguanidine derivatives and pharmaceutically acceptable salts thereof.

It is another object of the present invention to provide a method for preparing benzothiophen-2-carbonylguanidine derivatives.

It is a further object of the present invention to provide a pharmaceutical composition containing a benzothiophen-2-carbonylguanidine derivative or a pharmaceutically acceptable salt thereof as an effective ingredient for the prevention and treatment of ischemic heart diseases and ischemic cerebral diseases, and cardioprotectives in reperfusion therapy.

Technical Solution

In accordance with an aspect of the present invention, benzothiophen-2-carbonylguanidine derivatives and pharmaceutically acceptable salts thereof are provided.

In accordance with another aspect of the present invention, a method of preparing the benzothiophen-2-carbonylguanidine derivatives is provided.

In accordance with a further aspect of the present invention, a pharmaceutical composition containing a benzothiophen-2-carbonylguanidine derivative or a pharmaceutically acceptable salt thereof as an effective ingredient for the prevention and treatment of ischemic heart diseases and ischemic cerebral diseases, and cardioprotectives in reperfusion therapy is provided.

Advantageous Effects

The benzothiophen-2-carbonylguanidine derivatives of the present invention are found to have potent inhibitory activity against the sodium/hydrogen exchanger NHE-1, promote the functional recovery of ischemia/reperfusion-induced heart injury in isolated ischemic heart models, and significantly reduce the myocardiac infarct size in in vivo ischemic animal models, thereby showing excellent cardioprotective effects. In addition, the compounds protect neurons from necrosis and apoptosis and significantly reduce infarct sizes in in vivo ischemic brain models.

Consequently, the pharmaceutical compositions of the present invention as well as the compounds can be effectively used for the prevention and treatment of ischemic heart diseases such as myocardiac infarction, arrhythmia, angina pectoris and the like, and cerebrovascular diseases such as cerebral stroke and the like and be used as cardioprotective agents for the patients undergoing reperfusion therapy using chemicals such as thrombolytic agents, or surgery such as coronary artery bypass and percutaneous transluminal coronary angioplasty.

BEST MODE

The present invention pertains to benzothiophen-2-carbonylguanidine derivatives represented by the following Formula 1, and pharmaceutically acceptable salts thereof:

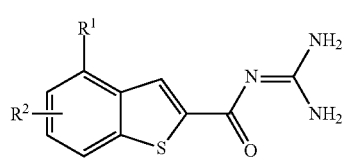

<Formula 1> wherein, $R^1$ is H, F, Cl, Br, I, CN, $NO_2$, amino, or branched or straight $C_1$~$C_5$ alkyl, $C_1$~$C_5$ alkenyl, $C_1$~$C_5$ alkynyl, $C_1$~$C_5$ alkoxy, $C_1$~$C_5$ haloalkyl, or $C_6$~$C_{14}$ aryl, the $C_6$~$C_{14}$ aryl being non-substituted or substituted with one selected from the group consisting of F, Cl, Br, I, CN, $NO_2$, amino, and branched or straight $C_1$~$C_5$ alkyl, $C_1$~$C_5$ alkenyl, $C_1$~$C_5$ alkynyl, $C_1$~$C_5$ alkoxy, and $C_1$~$C_5$ haloalkyl;

$R^2$ is H, F, Cl, Br, I, CN, $NO_2$, amino, or branched or straight $C_1$~$C_5$ alkyl, $C_1$~$C_5$ alkenyl, $C_1$~$C_5$ alkynyl, $C_1$~$C_5$ alkoxy, or $C_1$~$C_5$ haloalkyl.

In Formula 1, preferably, $R^1$ is H, F, Cl, Br, I, CN, $NO_2$, $NH_2$, $CF_3$, $OCH_3$, branched or straight $C_1$~$C_3$ alkyl, $C_1$~$C_3$ alkenyl, or $C_6$~$C_{10}$ aryl, the $C_6$~$C_{10}$ aryl being non-substituted or substituted with one selected from the group consisting of F, Cl, Br, I, CN, $NO_2$, $NH_2$, $CF_3$, $OCH_3$, branched or straight $C_1$~$C_3$ alkyl, and $C_1$~$C_3$ alkenyl; and $R^2$ is H, or $C_1$~$C_3$ alkyl.

Herein, the term "alkoxy" as used means an oxygen radical substituted with branched or straight alkyl, alkenyl or alkynyl.

The term "haloalkyl" as used herein means alkyl substituted with at least one of the atoms among fluorine, chlorine, bromine and iodine.

The term "amino" as used herein means —$NH_2$, —$NHR_3$ or —$NR_3R_4$ wherein $R_3$ and $R_4$ are independently straight or branched $C_1$~$C_5$ alkyl.

The benzothiophen-2-carbonylguanidine derivatives of the present invention, represented by the Formula 1, may be used in the form of pharmaceutically acceptable salts prepared from pharmaceutically acceptable free acids. The free acids may be inorganic or organic acid. Examples of useful inorganic acids include hydrochloric acid, hydrobromic acid, sulfuric acid and phosphoric acid, preferably hydrochloric acid. As organic acids, citric acid, lactic acid, maleic acid, fumaric acid, gluconic acid, methane sulfonic acid, acetic acid, glyconic acid, succinic acid, tartaric acid, 4-toluenesulfonic acid, galacturonic acid, embonic acid, glutamic acid or aspartic acid may be used, preferably methane sulfonic acid.

Also, the benzothiophen-2-carbonylguanidine derivatives of the present invention, represented by Formula 1, may be in the form of conventionally producible salts, hydrates, and solvates thereof as well as pharmaceutically acceptable salts.

Addition salts according to the present invention may be prepared using a conventional method. For example, they may be prepared by dissolving the compound of Formula 1 in a water-miscible organic solvent, such as acetone, methanol, ethanol or acetonitrile and adding an excess of organic acids or an excess of aqueous inorganic acid solutions so as to precipitate or crystallize salts. These addition salts may be obtained by distilling the solvent or excess of acids from the solution or by suctioning and filtering the precipitates.

More preferably, benzothiophen-2-carbonylguanidine derivatives or salts thereof include the following compounds:
1) (4-bromobenzothiophen-2-carbonyl)guanidine methane sulfonate,
2) [4-(2-chlorophenyl)benzothiophen-2-carbonyl]guanidine methanesulfonate,
3) [4-(3-chlorophenyl)benzothiophen-2-carbonyl]guanidine methanesulfonate,
4) [4-(4-chlorophenyl)benzothiophen-2-carbonyl]guanidine methanesulfonate,
5) [4-(2-fluorophenyl)benzothiophen-2-carbonyl]guanidine methanesulfonate,
6) [4-(3-fluorophenyl)benzothiophen-2-carbonyl]guanidine methanesulfonate,
7) [4-(4-fluorophenyl)benzothiophen-2-carbonyl]guanidine methanesulfonate,
8) [4-(2-methylphenyl)benzothiophen-2-carbonyl]guanidine methanesulfonate,
9) [4-(3-methylphenyl)benzothiophen-2-carbonyl]guanidine methanesulfonate,
10) [4-(4-methylphenyl)benzothiophen-2-carbonyl]guanidine methanesulfonate,
11) [4-(2-methoxyphenyl)benzothiophen-2-carbonyl]guanidine methanesulfonate,
12) [4-(3-methoxyphenyl)benzothiophen-2-carbonyl]guanidine methanesulfonate,
13) [4-(4-methoxyphenyl)benzothiophen-2-carbonyl]guanidine methanesulfonate,
14) [4-(2-trifluoromethylphenyl)benzothiophen-2-carbonyl]guanidine methanesulfonate,
15) [4-(3-trifluoromethylphenyl)benzothiophen-2-carbonyl]guanidine methanesulfonate,
16) [4-(4-trifluoromethylphenyl)benzothiophen-2-carbonyl]guanidine methanesulfonate,
17) (4-phenylbenzothiophen-2-carbonyl)guanidine methane sulfonate,
18) [4-(1-naphthalenyl)benzothiophen-2-carbonyl]guanidine methanesulfonate,
19) [4-(3,5-dichlorophenyl)benzothiophen-2-carbonyl]guanidine methanesulfonate,
20) [4-(2,5-dichlorophenyl)benzothiophen-2-carbonyl]guanidine, 21) [4-(2,3-dichlorophenyl)benzothiophen-2-carbonyl]guanidine methanesulfonate,
22) [4-(2-methoxy-5-chlorophenyl)benzothiophen-2-carbonyl]guanidine methanesulfonate,
23) [4-(3-chloro-4-fluorophenyl)benzothiophen-2-carbonyl]guanidine methanesulfonate,
24) [4-(3,5-difluorophenyl)benzothiophen-2-carbonyl]guanidine methanesulfonate,
25) [4-(2,5-difluorophenyl)benzothiophen-2-carbonyl]guanidine methanesulfonate,
26) [4-(2,3-difluorophenyl)benzothiophen-2-carbonyl]guanidine methanesulfonate,
27) [4-(3,4-difluorophenyl)benzothiophen-2-carbonyl]guanidine methanesulfonate,
28) [4-(2-methyl-5-fluorophenyl)benzothiophen-2-carbonyl]guanidine methanesulfonate,
29) [4-(2-fluoro-5-methylphenyl)benzothiophen-2-carbonyl]guanidine methanesulfonate,
30) [4-(3,5-dimethylphenyl)benzothiophen-2-carbonyl]guanidine methanesulfonate,
31) [4-(2,5-dimethylphenyl)benzothiophen-2-carbonyl]guanidine methanesulfonate,
32) (4-chlorobenzothiophen-2-carbonyl)guanidine methane sulfonate,
33) (4-fluorobenzothiophen-2-carbonyl)guanidine methane sulfonate,
34) (4-iodobenzothiophen-2-carbonyl)guanidine methane sulfonate,
35) (4-methylbenzothiophen-2-carbonyl)guanidine methane sulfonate,
36) (4-vinylbenzothiophen-2-carbonyl)guanidine methane sulfonate,
37) (4-ethylbenzothiophen-2-carbonyl)guanidine methane sulfonate,
38) (4-isopropylbenzothiophen-2-carbonyl)guanidine methane sulfonate,
39) (4-nitrobenzothiophen-2-carbonyl)guanidine methane sulfonate,
40) (4-aminobenzothiophen-2-carbonyl)guanidine methane sulfonate,
41) (4-methoxybenzothiophen-2-carbonyl)guanidine methane sulfonate,
42) (4-cyanobenzothiophen-2-carbonyl)guanidine methane sulfonate,
43) (4-trifluoromethylbenzothiophen-2-carbonyl)guanidine methanesulfonate,
44) (benzothiophen-2-carbonyl)guanidine methanesulfonate,
45) (4-bromo-5-methylbenzothiophen-2-carbonyl)guanidine methanesulfonate,
46) (4-chloro-5-methylbenzothiophen-2-carbonyl)guanidine methanesulfonate,
47) (4,5-dimethylbenzothiophen-2-carbonyl)guanidine methane sulfonate,
48) (4-cyano-5-methylbenzothiophen-2-carbonyl)guanidine methanesulfonate,
49) (4-bromo-6-methylbenzothiophen-2-carbonyl)guanidine methanesulfonate,
50) (4,6-dimethylbenzothiophen-2-carbonyl)guanidine methane sulfonate, and
51) (4-cyano-6-methylbenzothiophen-2-carbonyl)guanidine methanesulfonate.

Also, the present invention provides a method for the preparation of benzothiophen-2-carbonylguanidine derivatives and pharmaceutically acceptable salts thereof.

In accordance with an embodiment of the present invention, a method for preparing the benzothiophen-2-carbonylguanidine derivatives of Formula 1, as represented by Scheme 1, is provided.

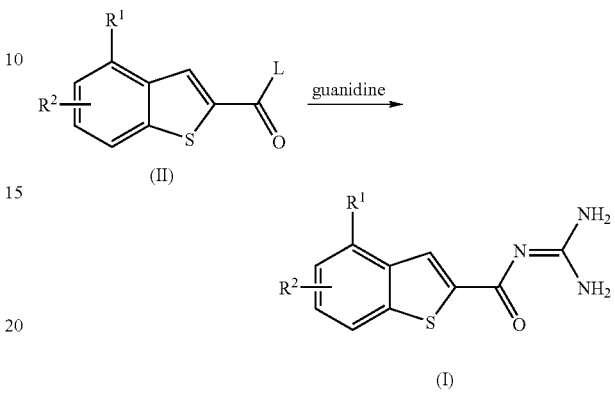

wherein, $R^1$ and $R^2$ are as defined in Formula 1;

L is a leaving group that is readily substitutable with guanidine and is selected from among halogen, alkoxy, aryloxy, sulfonyloxy, and carbonyloxy, preferably halogen, alkoxy, tosylate (—$OSO_2PhCH_3$), or mesylate (—$OSO_2CH_3$).

In Scheme 1, the carboxylic acid derivative (II) may be ester, acyl halide, or acid anhydride depending on the leaving group L. Examples of the ester derivative include active ester derivatives (e.g., p-nitrophenyl ester, N-hydroxysuccinimide ester, pentafluorophenyl ester), or sulfonate ester (tosylate ester, mesylate ester) in addition to general alkyl esters (e.g., methyl ester, ethyl ester). These carboxylic acid derivatives may be readily prepared from carboxylic acids using a typical method well known in the art.

In Scheme 1, 1) when the carboxylic acid derivative (II) is an alkyl ester or an active ester, it is allowed to react with a proper amount of, or an excess of, guanidine in a suitable solvent to afford the compound (I).

The solvent suitable for this reaction may be selected from among alcohols, such as methanol, ethanol or isopropanol, ethers, such as tetrahydrofuran, dioxane, 1,2-dimethoxyethane, and dimethylformamide (DMF), and mixtures thereof. The reaction is conducted at the temperature raging from room temperature to the boiling point of the solvent used.

2) When the carboxylic acid derivative (II) is an acyl halide or an acid anhydride, it is allowed to react with an excess of guanidine in a suitable solvent or with guanidine in the presence of a base to afford the compound (I). An inorganic base, such as sodium hydroxide, potassium hydroxide, sodium carbonate, etc., or an organic base, such as triethyl amine, pyridine, etc., may be suitable for use in this reaction.

As the reaction solvent, an aromatic hydrocarbon solvent such as benzene, toluene, etc., an ether solvent such as tetrahydrofuran, a halogenated hydrocarbon solvent such as dichloromethane, chloroform, etc., dimethylformamide (DMF), or combinations thereof may be used.

The carboxylic acid derivative (II), used as the starting material in Scheme 1, is prepared as follows.

1) In the case where the carboxylic acid derivative (II) in Scheme 1 is a general alkyl ester, such as methyl or ethyl ester (L=OMe or OEt) and $R^1$ is H, halogen (Br, Cl, F, I), CN, $NO_2$, $NH_2$, amino, haloalkyl, or alkoxy.

When $R^1$ of the carboxylic acid derivative (II) used in Scheme 1 is hydrogen, halogen (Br, Cl, F, I), cyano, nitro, amino, haloalkyl, or alkoxy, a compound (IV) is fomylated to give an aldehyde compound (V) which is subjected to a nucleophilic substitution reaction with methyl thioglycolate and subsequently to an intramolecular cyclization reaction, in order to produce the compound (II-1), as described in the following Scheme 2.

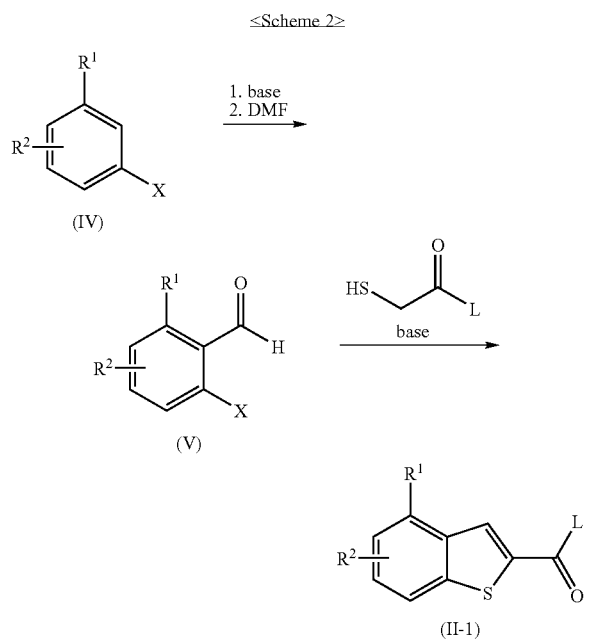

wherein,
$R^1$ is H, halogen (Br, Cl, F, I), CN, $NO_2$, amino, $C_1\sim C_5$ haloalkyl, or $C_1\sim C_5$ alkoxy;
$R^2$ is as defined in Formula 1;
L is as defined in Scheme 1; and
X is F, $NO_2$, Cl, or Br.

The aldehyde compound (V) used in Scheme 2 may be a commercially available compound or may be prepared from the compound (IV) having suitably substituted $R^1$, $R^2$ and X using a base. In latter case, the base, such as lithium diisopropylamide (LDA) or n-butyl lithium, is used to eliminate the proton from the carbon atom positioned between $R^1$ and X-substituted carbon atoms, and the negative charge thus produced attacks dimethylformamide (DMF) or methyl formate to introduce an aldehyde group thereinto, as known in the art.

The compound (V) undergoes a nucleophilic substitution reaction in the presence of a base, in which the nucleophilic attack of the thiol group of methyl thioglycolate on the carbon atom substituted with X, that is, halogen (F, Cl, Br) or nitro, occurs, so that methyl thioglycolate is added thereto while the X group is removed therefrom. Subsequently, there occurs an intramolecular cyclization reaction in which the alpha hydrogen of ester is eliminated and the negative charge thus formed attacks the aldehyde, followed by dehydration. That is, the benzothiophene ring compound (II-1) is prepared from the compound (V) via a sequence of nucleophilic substitution, intraomolecular cyclization and dehydration. The base suitable for these reactions is preferably potassium carbonate, potassium t-butoxide or sodium hydride. The serial reactions are preferably conducted in DMF or an ether solvent such as tetrahydrofuran or dioxane at a temperature ranging from room temperature to the boiling point of the solvent used.

In Scheme 2, the compound having an amino group as $R^1$ may be prepared from a compound (II-1) having a nitro group as $R^1$ by a typical reduction process.

In Scheme 2, a compound (II-5) having CN as $R^1$ may be prepared from a compound (II-4) having Br or I as $R^1$, as illustrated in Scheme 3.

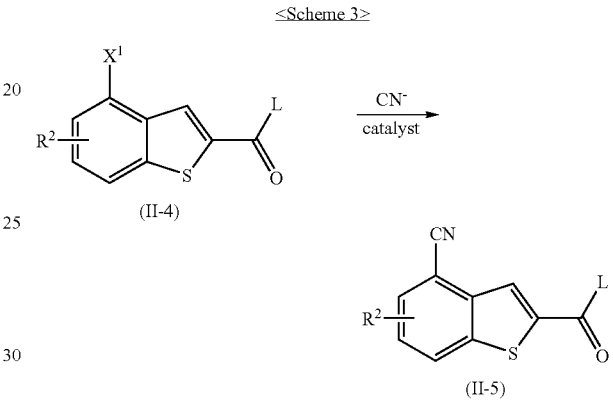

wherein,
$R^2$ is as defined in Formula 1;
L is as defined in Scheme 1;
$X^1$ is Br or I.

In Scheme 3, CuCN, KCN, or NaCN may be used as a source of $CN^-$, preferably CuCN.

This reaction may be performed in the absence of a catalyst by heating in a high-boiling point solvent, such as DMF or 1-methyl-2-pyrrolidinone, or in a microwave reactor. The reaction temperature is allowed to range from 100 to 220° C.

If used, palladium is preferred as a catalyst. $Pd_2(dba)_3$ or $Pd(PPh_3)_4$ is more preferable as a catalyst. In order to promote the reaction in combination with the catalyst, dppf (1,1'-bis (diphenylphosphino)ferrocene), $Et_4NCN$, or $Bu_3SnCl$ may be used. When a palladium catalyst is employed, an ether, such as dioxane or tetrahydrofuran, an aromatic hydrocarbon, such as benzene or toluene, $CH_3CN$, or DMF may be used, alone or in combination, as a solvent. The reaction temperature is allowed to range from room temperature to the boiling point of the solvent used.

2) In the case where the carboxylic acid derivative (II) in Scheme 1 is a general alkyl ester, such as methyl or ethyl ester (L=OMe or OEt) and $R^1$ is alkyl, alkenyl, alkynyl or aryl.

When the carboxylic acid derivative (II) used in Scheme 1 is a methyl or ethyl ester compound (L=$OCH_3$ or OEt) and $R^1$ is alkyl, alkenyl, alkynyl or aryl, a 4-halobenzothiophene compound (II-6) prepared using Scheme 2 is allowed to undergo a Stille-type or Suzuki-type coupling reaction with aryl and alkylboronic acid, or stanylaryl and an alkyl derivative compound (VI) in the presence of a metal catalyst, particularly palladium, to yield compounds (II-7) and (II-8), as illustrated in the following Scheme 4:

Scheme 4

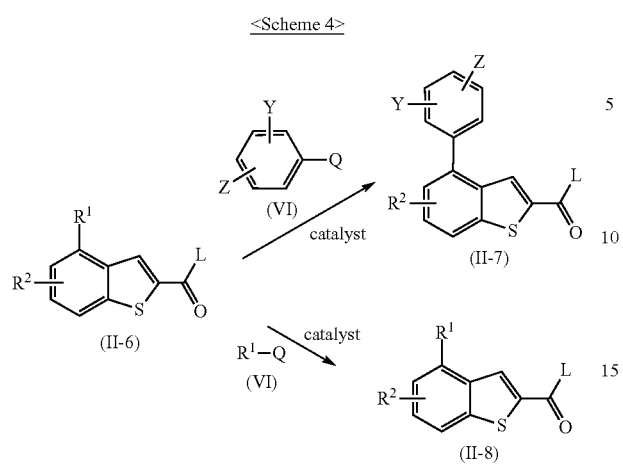

wherein,
L is as defined in Scheme 1;
$X^1$ is Br, I, or Cl;
Y and Z are independently H, halogen, CN, $NO_2$, amino, branched or straight $C_1\sim C_5$ alkyl, $C_1\sim C_5$ alkenyl, $C_1\sim C_5$ alkynyl, $C_1\sim C_5$ alkoxy, or $C_1\sim C_5$ haloalkyl;
$R^1$ is branched or straight $C_1\sim C_5$ alkyl, $C_1\sim C_5$ alkenyl, $C_1\sim C_5$ alkynyl or $C_6\sim C_{14}$ aryl, the $C_6\sim C_{14}$ aryl being non-substituted or substituted with one selected from the group consisting of F, Cl, Br, I, CN, $NO_2$, an amino group, and branched or straight $C_1\sim C_5$ alkyl, $C_1\sim C_5$ alkenyl, $C_1\sim C_5$ alkynyl, $C_1\sim C_5$ alkoxy, and $C_1\sim C_5$ haloalkyl; and
$R^2$ is as defined in Formula 1;
Q is $B(OH)_2$, $BCl_2$, $BBr_2$,

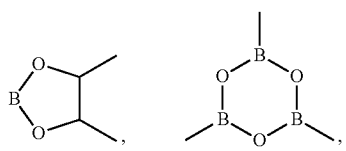

$SnBU_3$, $SnMe_3$, or ZnCl.

In Scheme 4, boronic acid or a stanyl compound of General Formula (VI) may be a commercially available compound or may be prepared from a halide compound according to a method known in the art.

Examples of the metal catalyst useful for Scheme 4 include palladium, nickel, and platinum complexes, with palladium being preferred. As a palladium catalyst, $Pd(PPh_3)_4$, Pd—C, $PdCl_2(PPh_3)_2$, $Pd_2(dba)_3$, $PdCl_2(dppf)$, $[PdCl(allyl)]_2$, $Pd(OAc)_2$ or $PdCl_2$ may be used.

In Scheme 4, a phosphine such as $PPh_3$, P-(o-tolyl)$_3$, or $PBu_3$, or a salt such as lithium chloride, lithium bromide or lithium iodide may be used as an additive in order to promote the reaction and increase the production yield.

The base is used in an amount of 1 to 3 equivalents for the Suzuki-type reaction in Scheme 4. A tertiary amine organic base such as triethylamine and isopropylethylamine, or an inorganic base such as sodium carbonate, potassium carbonate, potassium hydroxide, sodium hydroxide, cesium carbonate, barium hydroxide, and the like is useful. If an inorganic base is insoluble in an organic solvent, it may be added as a 0.5 to 4 M aqueous solution.

For the reaction in Scheme 4, an ether such as tetrahydrofuran, dioxane, 1,2-dimethoxyethane, an aromatic such as benzene, toluene, xylene, etc., an alcohol solvent such as methanol, ethanol, etc., DMF, acetonitryl, or ethylacetate may be used, alone or in combination, as a solvent. The reaction is conducted at a temperature ranging from room temperature to the boiling point of the solvent used.

In Scheme 4, a compound having ethyl as $R^1$ may be prepared from a compound having vinyl as $R^1$ by a typical reduction method.

In accordance with another aspect, the present invention provides a method of preparing the benzothiophen-2-carbonylguanidine derivatives of Formula 1, as illustrated in the following Scheme 5:

Scheme 5

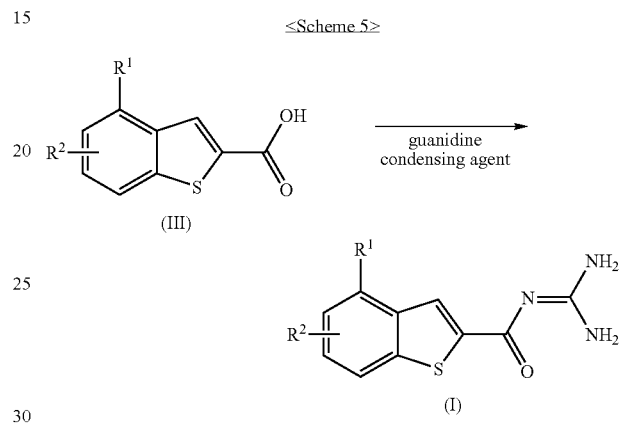

wherein, $R^1$ and $R^2$ are independently as defined in Formula 1.

In Scheme 5, the carboxylic acid compound (III) is reacted with guanidine in the presence of a condensing agent to produce a benzothiophen-2-carbonylguanidine compound (I).

In Scheme 5, the carboxylic acid compound (III) may react with an equivalent or an excess of guanidine in the presence of a condensing agent in a suitable solvent to yield the compound (I). This reaction is conducted at a temperature ranging from room temperature to the boiling point of the solvent used.

N,N-carbonyldiimidazole, dicyclohexylcarbodiimide (DCC), diisopropylcarbodiimide (DIPC), 1-ethyl-3-(3-dimethyl aminopropyl)carbodiimide (WSC), or diphenylphosphonylazide (DPPA) may be used as the condensing agent.

In this reaction, an ether such as tetrahydrofuran or 1,4-dioxane, an aromatic hydrocarbon such as benzene or toluene, a halogenated hydrocarbon such as dichloromethane or chloroform, or DMF may be used, alone or in combination, as a solvent.

The carboxylic acid compound (III), the starting material of Scheme 5, may be prepared by hydrolyzing the ester prepared using Schemes 2 to 4 in the presence of a base in a typical process well known in the art.

Among carboxylic acid derivatives (II) in Scheme 1, compounds other than methyl or ethyl ester compounds may be prepared from the carboxylic acid compound (III) of Scheme 5 using a typical method well known in the art.

Also, the present invention provides a pharmaceutical composition for use in the prevention and treatment of ischemic heart and cerebral diseases and cardioprotection in reperfusion therapy, containing the benzothiophen-2-carbonylguanidine derivatives or pharmaceutically acceptable salts thereof as an effective ingredient.

The compound of the present invention may be clinically administered in oral or non-oral forms. It is usually formulated in combination with a diluent or excipient, such as a filler, a thickening agent, a binder, a wetting agent, a disintegrant, a surfactant, etc. Solid agents intended for oral administration of the compound of the present invention may be in the form of tablets, pills, powders, granules, capsules, troches, and the like. These solid agents are formulated in combination with at least one excipient such as starch, calcium carbonate, sucrose, lactose, or gelatine. Besides, a lubricant such as magnesium stearate, talc, and the like may be added, as well. Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid agents for the oral administration of the compound of the present invention. Also, the compound of the present invention may be administered via a non-oral route. For this, sterile aqueous solutions, non-aqueous solvents, suspensions, emulsions, lyophilics, suppositories, and the like may be used. Injectable propylene glycol, polyethylene glycol, vegetable oils such as olive oil, and esters such as ethyl olate may be suitable for non-aqueous solvents and suspensions. The basic materials of -suppositories include witepsol, macrogol, tween 61, cacao paper, laurin paper, glycerol, and gelatine.

Depending on the conditions of patients, including age, body weight, sex, administration route, health state, and disease severity, the administration dose of the compound of the present invention to humans may vary. Typically, the compound of the present invention is administered at a dose from 0.1 to 1,000 mg a day for an adult weighing 70 kg, and preferably at a dose from 1 to 500 mg a day. The compound may be administered in a single dose or in divided doses per day according to the instruction of the physician or pharmacist.

The benzothiophen-2-carbonylguanidine derivatives, along with pharmaceutically acceptable salts thereof according to the present invention, is found to have potent inhibitory effect on NHE-1 as demonstrated in human NHE-1 expressed cells, effectively protect the heart from ischemia/reperfusion injury by recovering cardiac functions (left ventricular diastolic pressure) in an isolated ischemic rat heart model of Langendorff, and show excellent anti-ischemic activity by significantly reducing the infarction size in an ischemic myocardial infarction model of an anesthetized rat.

Furthermore, the benzothiophen-2-carbonylguanidine derivatives and pharmaceutically acceptable salts thereof according to the present invention show the great protective effect on glutamate-induced damage and necrosis of cerebral cortical neurons isolated from the fetal rat brain, and an excellent anti-ischemic effect by reducing the size of cerebral infarction in an ischemic brain model.

Having potent inhibitory effect against NHE-1, and excellent protective effects on neuronal cell damage and on both the heart and the brain against ischemia/reperfusion injury in in-vivo and in-vitro models, therefore, the compounds of the present invention can be used for the prevention and treatment of ischemic cardiac diseases such as myocardiac infarction, arrhythmia, and angina pectoris and ischemic cerebral diseases such as ischemic stroke, and can serve as a cardioprotective agent applicable to the patients undergoing coronary reperfusion therapy including coronary artery bypass, percutaneous transluminal coronary angioplasty, and/or thrombolytics for myocardiac infarction.

[Mode for Invention]

A better understanding of the present invention may be obtained through the following examples and experimental examples which are set forth to illustrate, but are not to be construed as the limit of the present invention.

In the present invention, molecular structures of compounds were confirmed using infrared spectroscopy, NMR spectroscopy, mass spectroscopy, liquid chromatography, X-ray crystallography, optical rotation spectroscopy, and elemental analysis for comparing calculated values of representative elements with experimentally observed values thereof.

The compound (II) of Reactions 1~5 was prepared via the following preparative examples.

PREPARATIVE EXAMPLE 1

Preparation of
4-Bromobenzothiophene-2-Carboxylic Acid Methyl Ester (Step 1) Preparation of 2,6-Dibromo Benzaldehyde To anhydrous THF (70 ml), diisopropylamine (8.3 ml, 59.34 mmol) was added and then n-BuLi (1.6 M, 59.34 mmol) was slowly added dropwise at 0° C. using a syringe in a nitrogen atmosphere. The reaction mixture was stirred at 0° C. for 30 min, and the temperature thereof was cooled to −78° C. Subsequently, 1,3-dibromobenzene (7 g, 29.67 mmol) in THF (35 ml) was slowly added using a dropping funnel. The reaction mixture was stirred at −78° C. for 30 min, following the slow addition of DMF (4.6 ml, 59.34 mmol), and then continuously stirred for 1 hour. After the termination of the reaction, an aqueous solution of dilute $H_2SO_4$ was added, and the resulting solution was extracted two times with ethyl acetate, washed with a saturated NaCl solution, dried over anhydrous $MgSO_4$, and then filtered. The filtrate was concentrated under reduced pressure, and the residue was purified by silica gel column chromatography (hexane:ethyl acetate=40:1), thus obtaining the title compound as a white solid (6.64 g, 25.16 mmol, 85%).

$^1$H NMR(200 MHz, $CDCl_3$) δ 10.26(s, 1H), 7.63(d, 2H), 7.22(t, 1H)

MS(m/z)$M^+$=263 ($M^+$)

(Step 2) Preparation of
4-Bromobenzothiophene-2-Carboxylic Acid Methyl Ester

To the solution of the compound (6.64 g, 25.16 mmol) obtained in Step 1 in DMF (90 ml), potassium carbonate (7.65 g, 55.35 mmol) and methyl thioglycolate (2.7 ml, 30.19 mmol) were added in that order, and then the reaction mixture was heated at reflux with stirring for 6 hours. After the termination of the reaction, the resulting reaction solution was cooled to room temperature, extracted with ethyl acetate, and then washed with water and brine. Subsequently, the reaction solution was dried over $MgSO_4$, and then filtered. The filtrate was concentrated under reduced pressure, and the residue was purified by silica gel column chromatography (hexane:ethyl acetate=40:1), thus obtaining the title compound as a white solid (5.72 g, 21.09 mmol, 84%).

$^1$H NMR(200 MHz, $CDCl_3$) δ 8.19(s, 1H), 7.79(d, 1H, J=8.2 Hz), 7.58(d, 1H, J=7.6 Hz), 7.30(dd, 1H, J=7.6, 8.2 Hz), 3.96(s, 3H)

MS(m/z)$M^+$=272 ($M^+$)

PREPARATIVE EXAMPLE 2

Preparation of
4-(2-Chlorophenyl)Benzothiophene-2-Carboxylic
Acid Methyl Ester

4-Bromobenzothiophene-2-carboxylic acid methyl ester (150 mg, 0.55 mmol), obtained in Preparative Example 1, $Pd(PPh_3)_4$ (102 mg, 8 mmol %), and 2-chlorophenyl boronic acid (130 mg, 0.83 mmol) were dissolved in toluene (3 ml), after which the reaction solution was added with 2M $K_2CO_3$ (0.55 ml, 1.1 mmol) and then heated to reflux with stirring for 16 hours. After the termination of the reaction, the resulting reaction solution was extracted two times with ethyl acetate, washed with brine, dried over $MgSO_4$, and then filtered. The filtrate was concentrated under reduced pressure, and the residue was purified by silica gel column chromatography (hexane→hexane:ethyl acetate=60:1), thus obtaining the title compound as a white solid (144 mg, 0.47 mmol, 86%).

$^1$H NMR(200 MHz, $CDCl_3$) δ 7.87(d, 1H, J=8.2 Hz), 7.76 (s, 1H), 7.57~7.32(m, 6H), 3.90 (s, 3H)

PREPARATIVE EXAMPLE 3

Preparation of
4-(3-Chlorophenyl)Benzothiophene-2-Carboxylic
Acid Methyl Ester

The title compound was prepared as a white solid (162 mg, 0.54 mmol, 73%) using the same procedure as in Preparative Example 2, with the exception that 3-chlorophenyl boronic acid (173 mg, 1.11 mmol) was used.

$^1$H NMR(300 MHz, $CDCl_3$) δ 8.09(s, 1H), 7.87(d, 1H, J=8.1 Hz), 7.55~7.35(m, 6H), 3.94(s, 3H)

MS(m/z)M$^+$=302 (M$^+$)

PREPARATIVE EXAMPLE 4

Preparation of
4-(4-Chlorophenyl)Benzothiophene-2-Carboxylic
Acid Methyl Ester

The title compound was prepared as a white solid (178 mg, 0.62 mmol, 84%) using the same method as in Preparative Example 2, with the exception that 4-chlorophenyl boronic acid (260 mg, 1.66 mmol) was used.

$^1$H NMR(200 MHz, $CDCl_3$) δ 8.09(s, 1H), 7.86(d, 1H, J=8.2 Hz), 7.56~7.34(m, 6H), 3.93(s, 3H)

MS(m/z)M$^+$=302 (M$^+$)

PREPARATIVE EXAMPLE 5

Preparation of
4-(2-Fluorophenyl)Benzothiophene-2-Carboxylic
Acid Methyl Ester

The title compound was prepared as a white solid (233 mg, 0.81 mmol, 74%) using the same method as in Preparative Example 2, with the exception that 2-fluorophenyl boronic acid (232 mg, 1.66 mmol) was used.

$^1$H NMR(200 MHz, $CDCl_3$) δ 7.93(m, 2H), 7.88~7.19(m, 6H), 3.91(s, 3H)

MS(m/z)M$^+$=286 (M$^+$)

PREPARATIVE EXAMPLE 6

Preparation of
4-(3-Fluorophenyl)Benzothiophene-2-Carboxylic
Acid Methyl Ester

The title compound was prepared as a pale yellow solid (135 mg, 0.47 mmol, 70%) using the same method as in Preparative Example 2, with the exception that 3-fluorophenyl boronic acid (191 mg, 1.36 mmol) was used.

$^1$H NMR(200 MHz, $CDCl_3$) δ 8.12(s, 1H), 7.85(d, 1H, J=8.4 Hz), 7.56~7.08(m, 6H), 3.93(s, 3H)

MS(m/z)M$^+$=286 (M$^+$)

PREPARATIVE EXAMPLE 7

Preparation of
4-(4-Fluorophenyl)Benzothiophene-2-Carboxylic
Acid Methyl Ester

The title compound was prepared as a pale yellow solid (178 mg, 0.62 mmol, 84%) using the same method as in Preparative Example 2, with the exception that 4-fluorophenyl boronic acid (155 mg, 1.11 mmol) was used.

$^1$H NMR(200 MHz, $CDCl_3$) δ 8.09(s, 1H), 7.83(d, 1H, J=8.1 Hz), 7.55~7.15(m, 6H), 3.92(s, 3H)

MS(m/z)M$^+$=286 (M$^+$)

PREPARATIVE EXAMPLE 8

Preparation of
4-(2-Methylphenyl)Benzothiophene-2-Carboxylic
Acid Methyl Ester

The title compound was prepared as a white solid (280 mg, 0.99 mmol, 90%) using the same method as in Preparative Example 2, with the exception that 2-methylphenyl boronic acid (226 mg, 1.66 mmol) was used.

$^1$H NMR(200 MHz, $CDCl_3$) δ 7.87(d, 1H, J=8.4 Hz), 7.70 (s, 1H), 7.51(dd, 1H, J=7.2, 8.2 Hz), 7.36~7.21(m, 5H), 3.89 (s, 3H), 2.10(s, 3H)

MS(m/z)M$^+$=282 (M$^+$)

PREPARATIVE EXAMPLE 9

Preparation of
4-(3-Methylphenyl)Benzothiophene-2-Carboxylic
Acid Methyl Ester

The title compound was prepared as a white solid (290 mg, 1.03 mmol, 93%) using the same method as in Preparative Example 2, with the exception that 3-methylphenyl boronic acid (226 mg, 1.66 mmol) was used.

$^1$H NMR(300 MHz, $CDCl_3$) δ 8.15(s, 1H), 7.83(d, 1H, J=8.4 Hz), 7.51(dd, 1H, J=7.5, 8.1 Hz), 7.39~7.25(m, 5H), 3.92(s, 3H), 2.45(s, 3H)

MS(m/z)M$^+$=282 (M$^+$)

PREPARATIVE EXAMPLE 10

Preparation of
4-(4-Methylphenyl)Benzothiophene-2-Carboxylic
Acid Methyl Ester

The title compound was prepared as a white solid (205 mg, 0.73 mmol, 98%) using the same method as in Preparative Example 2, with the exception that 4-methylphenyl boronic acid (150 mg, 1.11 mmol) was used.
$^1$H NMR(200 MHz, CDCl$_3$) δ 8.16(s, 1H), 7.83(d, 1H, J=8.0 Hz), 7.54~7.25(m, 6H), 3.92(s, 3H), 2.45(s, 3H)
MS(m/z)M$^+$=282 (M$^+$)

PREPARATIVE EXAMPLE 11

Preparation of 4-(2-Methoxyphenyl)Benzothiophene-2-Carboxylic Acid Methyl Ester

The title compound was prepared as a white solid (299 mg, 1.00 mmol, 91%) using the same method as in Preparative Example 2, with the exception that 2-methoxyphenyl boronic acid (252 mg, 1.66 mmol) was used.
$^1$H NMR(200 MHz, CDCl$_3$) δ 7.86~7.82(m, 2H), 7.54~7.03(m, 6H), 3.90(s, 3H), 3.75(s, 3H)
MS(m/z)M$^+$=298 (M$^+$)

PREPARATIVE EXAMPLE 12

Preparation of 4-(3-Methoxyphenyl)Benzothiophene-2-Carboxylic Acid Methyl Ester

The title compound was prepared as a pale yellow solid (130 mg, 0.44 mmol, 59%) using the same method as in Preparative Example 2, with the exception that 3-methoxyphenyl boronic acid (135 mg, 1.11 mmol) was used.
$^1$H NMR(200 MHz, CDCl$_3$) δ 8.16(s, 1H), 7.87(d, 1H, J=8.1 Hz), 7.55~7.37(m, 3H), 7.15~6.96(m, 3H), 3.92(s, 3H), 3.87(s, 3H)
MS(m/z)M$^+$=298 (M$^+$)

PREPARATIVE EXAMPLE 13

Preparation of 4-(4-Methoxyphenyl)Benzothiophene-2-Carboxylic Acid Methyl Ester

The title compound was prepared as a white solid (320 mg, 1.07 mmol, 97%) using the same method as in Preparative Example 2, with the exception that 4-methoxyphenyl boronic acid (252 mg, 1.66 mmol) was used.
$^1$H NMR(200 MHz, CDCl$_3$) δ 8.15(s, 1H), 7.79(d, 1H, J=8.1 Hz), 7.53~7.44(m, 3H), 7.35(d, 1H, J=7.4 Hz), 7.07~7.00(m, 2H), 3.92(s, 3H), 3.89(s, 3H)

PREPARATIVE EXAMPLE 14

Preparation of 4-(2-Trifluoromethylphenyl)Benzothiophene-2-Carboxylic Acid Methyl Ester The title compound was prepared as a white solid (170 mg, 0.51 mmol, 46%) using the same method as in Preparative Example 2, with the exception that 2-trifluoromethylphenyl boronic acid (315 mg, 1.66 mmol) was used.
$^1$H NMR(200 MHz, CDCl$_3$) δ 7.91~7.80(m, 2H), 7.63~7.45(m, 4H), 7.38~7.28(m, 2H), 3.89(s, 3H)
MS(m/z)M$^+$=336 (M$^+$)

PREPARATIVE EXAMPLE 15

Preparation of 4-(3-Trifluoromethylphenyl)Benzothiophene-2-Carboxylic Acid Methyl Ester The title compound was prepared as a white solid (360 mg, 1.07 mmol, 97%) using the same method as in Preparative Example 2, with the exception that 3-trifluoromethylphenyl boronic acid (315 mg, 1.66 mmol) was used.
$^1$H NMR(200 MHz, CDCl$_3$) δ 8.05(s, 1H), 7.91(d, 1H, J=8.1 Hz), 7.79~7.50(m, 5H), 7.38(d, 1H, J=7.4 Hz), 3.93(s, 3H)
MS(m/z)M$^+$=336 (M$^+$)

PREPARATIVE EXAMPLE 16

Preparation of 4-(4-Trifluoromethylphenyl)Benzothiophene-2-Carboxylic Acid Methyl Ester The title compound was prepared as a white solid (237 mg, 0.71 mmol, 95%) using the same method as in Preparative Example 2, with the exception that 4-trifluoromethylphenyl boronic acid (210 mg, 1.11 mmol) was used.
$^1$ NMR(2.00 MHz, CDCl$_3$) δ 8.08(s, 1H), 7.89(d, 1H J=8.0 Hz), 7.80~7.65(m, 4H), 7.55(dd, 1H, J=7.4, 8.2 Hz), 7.38(d, 1H, J=7.4 Hz), 3.93(s, 3H)
MS(m/z)M$^+$=336 (M$^+$)

PREPARATIVE EXAMPLE 17

Preparation of 4-Phenylbenzothiophene-2-Carboxylic Acid Methyl Ester

The title compound was prepared as a white solid (195 mg, 0.73 mmol, 98%) using the same method as in Preparative Example 2, with the exception that phenyl boronic acid (135 mg, 1.11 mmol) was used.
$^1$H NMR(200 MHz, CDCl$_3$) δ 8.15(s, 1H), 7.85(d, 1H, J=8.0 Hz), 7.56~7.37(m, 7H), 3.92(s, 3H)
MS(m/z)M$^+$=268 (M$^+$)

PREPARATIVE EXAMPLE 18

Preparation of 4-(1-Naphthalenyl)Benzothiophene-2-Carboxylic Acid Methyl Ester

The title compound was prepared as a white solid (172 mg, 0.54 mmol, 73%) using the same method as in Preparative Example 2, with the exception that 1-naphthalene boronic acid (190 mg, 1.11 mmol) was used.
$^1$H NMR(200 MHz, CDCl$_3$) δ 7.97~7.92(m, 3H), 7.62~7.26(m, 8H), 3.84(s, 3H)
MS(m/z)M$^+$=318 (M$^+$)

PREPARATIVE EXAMPLE 19

Preparation of 4-(3,5-Dichlorophenyl)Benzothiophene-2-Carboxylic Acid Methyl Ester 4-Bromobenzothiophene-2-carboxylic acid methyl ester (200 mg, 0.74 mmol), obtained in Preparative Example 1, Pd(PPh$_3$)$_4$ (68 mg, 8 mmol %), and 3,5-dichlorophenyl boronic acid (212 mg, 1.11 mmol) were dissolved in 1,2-dimethoxyethane (4.2 ml), and then 2M Ba(OH)$_2$.H$_2$O (210 mg, 1.11 mmol) was added. The reaction solution was heated to reflux with stirring for 16 hours, and was extracted two times with ethyl acetate, washed with brine, dried over MgSO$_4$, and then filtered. The filtrate was concentrated under reduced pressure, and the residue was purified by silica gel column chromatography (hexane→hexane:ethyl acetate=60:1), thus obtaining the title compound as a white solid (137 mg, 0.41 mmol, 55%).
$^1$H NMR(200 MHz, CDCl$_3$) δ 8.05(s, 1H), 7.89(d, 1H, J=8.4 Hz), 7.56~7.32(m, 5H), 3.95(s, 3H)
MS(m/z)M$^+$=336 (M$^+$)

PREPARATIVE EXAMPLE 20

Preparation of 4-(2,5-Dichlorophenyl)Benzothiophene-2-Carboxylic Acid Methyl Ester The title compound was prepared as a pale yellow solid (338 mg, 1.00 mmol, 91%) in the same manner as in Preparative Example 19, with the exception that 2,5-dichlorophenyl boronic acid (317 mg, 1.66 mmol) was used.
$^1$H NMR(200 MHz, CDCl$_3$) δ 7.92(d, 1H, J=8.2 Hz), 7.74 (s, 1H), 7.57~7.26(m, 5H), 3.92(s, 3H)
MS(m/z)M$^+$=336 (M$^+$)

PREPARATIVE EXAMPLE 21

Preparation of 4-(2,3-Dichlorophenyl)Benzothiophene-2-Carboxylic Acid Methyl Ester The title compound was prepared as a white solid (283 mg, 0.84 mmol, 76%) in the same manner as in Preparative Example 19, with the exception that 2,3-dichlorophenyl boronic acid (317 mg, 1.66 mmol) was used.
$^1$H NMR(200 MHz, CDCl$_3$) δ 7.93(d, 1H, J=8.2 Hz), 7.71 (s, 1H), 7.59~7.49(m, 2H), 7.35~7.26(m, 3H), 3.91(s, 3H)
MS(m/z)M$^+$=(M$^+$)

PREPARATIVE EXAMPLE 22

Preparation of 4-(2-Methoxy-5-Chlorophenyl)Benzothiophene-2-Carboxylic Acid Methyl Ester The title compound was prepared as a pale yellow solid (320 mg, 0.96 mmol, 87%) in the same manner as in Preparative Example 19, with the exception that 2-methoxy-5-chlorophenyl boronic acid (309 mg, 1.66 mmol) was used.
$^1$H NMR(500 MHz, CDCl$_3$) δ 7.89(d, 1H, J=8.0 Hz), 7.82 (s, 1H), 7.54(dd, 1H, J=7.7, 8.1 Hz), 7.36~7.30(m, 3H), 6.99 (d, 1H, J=8.7 Hz), 3.94(s, 3H), 3.78(s, 3H)
MS(m/z)M$^+$=332 (M$^+$)

PREPARATIVE EXAMPLE 23

Preparation of 4-(3-Chloro-4-Fluorophenyl)Benzothiophene-2-Carboxylic Acid Methyl Ester The title compound was prepared as a white solid (330 mg, 1.03 mmol, 93%) in the same manner as in Preparative Example 19, with the exception that 3-chloro-4-fluorophenyl boronic acid (289 mg, 1.66 mmol) was used.
$^1$H NMR(200 MHz, CDCl$_3$) δ 8.05(s, 1H), 7.88(d, 1H, J=8.0 Hz), 7.59~7.26(m, 5H), 3.93(s, 3H)
MS(m/z)M$^+$=320 (M$^+$)

PREPARATIVE EXAMPLE 24

Preparation of 4-(3,5-Difluorophenyl)Benzothiophene-2-Carboxylic Acid Methyl Ester The title compound was prepared as a white solid (280 mg, 0.92 mmol, 83%) in the same manner as in Preparative Example 19, with the exception that 3,5-difluorophenyl boronic acid (262 mg, 1.66 mmol) was used.
$^1$H NMR(200 MHz, CDCl$_3$) δ 8.10(s, 1H), 7.89(d, 1H, J=8.4 Hz), 7.53(dd, 1H, J=7.4, 8.0 Hz), 7.35(d, 1H, J=7.4 Hz), 7.09~7.04(m, 3H), 3.94(s, 3H)
MS(m/z)M$^+$=304 (M$^+$)

PREPARATIVE EXAMPLE 25

Preparation of 4-(2,5-Difluorophenyl)Benzothiophene-2-Carboxylic Acid Methyl Ester The title compound was prepared as a white solid (263 mg, 0.86 mmol, 78%) in the same manner as in Preparative Example 19, with the exception that 2,5-difluorophenyl boronic acid (262 mg, 1.66 mmol) was used.
$^1$H NMR(200 MHz, CDCl$_3$) δ 7.93~7.89(m, 2H), 7.54(dd, 1H, J=7.6, 8.0 Hz), 7.38(d, 1H, J=7.4 Hz), 7.25~7.10(m, 3H), 3.93(s, 3H)
MS(m/z)M$^+$=304 (M$^+$)

PREPARATIVE EXAMPLE 26

Preparation of 4-(2,3-Difluorophenyl)Benzothiophene-2-Carboxylic Acid Methyl Ester The title compound was prepared as a white solid (253 mg, 0.83 mmol, 75%) in the same manner as in Preparative Example 19, with the exception that 2,3-difluorophenyl boronic acid (262 mg, 1.66 mmol) was used.
$^1$H NMR(200 MHz, CDCl$_3$) δ 7.94~7.90(m, 2H), 7.54(dd, 1H, J=7.4, 8.0 Hz), 7.39(d, 1H, J=7.4 Hz), 7.30~7.18(m, 3H), 3.93(s, 3H)
MS(m/z)M$^+$=304 (M$^+$)

PREPARATIVE EXAMPLE 27

Preparation of 4-(3,4-Difluorophenyl)Benzothiophene-2-Carboxylic Acid Methyl Ester The title compound was prepared as a white solid (325 mg, 1.07 mmol, 97%) in the same manner as in Preparative Example 19, with the exception that 3,4-difluorophenyl boronic acid (262 mg, 1.66 mmol) was used.
$^1$H NMR(200 MHz, CDCl$_3$) δ 8.08(s, 1H), 7.86(d, 1H, J=8.0 Hz), 7.56~7.23(m, 5H), 3.94(s, 3H)
MS(m/z)M$^+$=304 (M$^+$)

PREPARATIVE EXAMPLE 28

Preparation of 4-(2-Methyl-5-Fluorophenyl)Benzothiophene-2-Carboxylic Acid Methyl Ester The title compound was prepared as a white solid (310 mg, 1.03 mmol, 93%) in the same manner as in Preparative Example 19, with the exception that 2-methyl-5-fluorophenyl boronic acid (256 mg, 1.66 mmol) was used.
$^1$H NMR(200 MHz, CDCl$_3$) δ 7.87(d, 1H, J=8.0 Hz), 7.68 (s, 1H), 7.51(dd, 1H, J=7.2, 8.2 Hz), 7.31~7.04(m, 4H), 3.90 (s, 3H), 2.04(s, 3H)
MS(m/z)M$^+$=300 (M$^+$)

PREPARATIVE EXAMPLE 29

Preparation of 4-(2-Fluoro-5-Methylphenyl)Benzothiophene-2-Carboxylic Acid Methyl Ester The title compound was prepared as a white solid (321 mg, 1.07 mmol, 97%) in the same manner as in Preparative Example 19, with the exception that 5-fluoro-2-methylphenyl boronic acid (256 mg, 1.66 mmol) was used.

$^1$H NMR(200 MHz, CDCl$_3$) δ 7.93~7.85(m, 2H), 7.52(dd, 1H, J=7.4, 7.4 Hz), 7.39(d, 1H, J=7.4 Hz), 7.26~7.05(m, 3H), 3.92(s, 3H), 2.39(s, 3H)

MS(m/z)M$^+$=300 (M$^+$)

PREPARATIVE EXAMPLE 30

Preparation of 4-(3,5-Dimethylphenyl)Benzothiophene-2-Carboxylic Acid Methyl Ester The title compound was prepared as a white solid (280 mg, 0.95 mmol, 85%) in the same manner as in Preparative Example 19, with the exception that 3,5-dimethylphenyl boronic acid (249 mg, 1.66 mmol) was used.

$^1$H NMR(200 MHz, CDCl$_3$) δ 8.19(s, 1H), 7.86(d, 1H, J=8.0 Hz), 7.53(dd, 1H, J=7.6, 8.0 Hz), 7.39(d, 1H, J=7.4 Hz), 7.18~7.12(m, 3H), 3.96(s, 3H), 2.44(s, 6H)

MS(m/z)M$^+$=296 (M$^+$)

PREPARATIVE EXAMPLE 31

Preparation of 4-(2,5-Dimethylphenyl)Benzothiophene-2-Carboxylic Acid Methyl Ester The title compound was prepared as a white solid (316 mg, 1.07 mmol, 96%) in the same manner as in Preparative Example 19, with the exception that 2,5-dimethylphenyl boronic acid (249 mg, 1.66 mmol) was used.

$^1$H NMR(200 MHz, CDCl$_3$) δ 7.84(d, 1H, J=8.4 Hz), 7.71 (s, 1H), 7.50(dd, 1H, J=7.4, 8.0 Hz), 7.26~7.05(m, 4H), 3.89 (s, 3H), 2.36(s, 3H), 2.04(s, 3H)

MS(m/z)M$^+$=296 (M$^+$)

PREPARATIVE EXAMPLE 32

Preparation of 4-Chlorobenzothiophene-2-Carboxylic Acid Methyl Ester

The title compound was prepared as a white solid (1.0 g, 4.39 mmol, 85%) in the same manner as in Step 2 of Preparative Example 1, with the exception that 2-chloro-6-nitro benzaldehyde (960 mg, 5.17 mmol) was used.

$^1$H NMR(200 MHz, CDCl$_3$) δ 8.22(s, 1H), 7.78~7.73(m, 1H), 7.43~7.33(m, 2H), 3.96(s, 3H)

MS(m/z)M$^+$=226 (M$^+$)

PREPARATIVE EXAMPLE 33

Preparation of 4-Fluorobenzothiophene-2-Carboxylic Acid Methyl Ester.

The title compound was prepared as a white solid (553 mg, 2.63 mmol, 66%) in the same manner as in Step 2 of Preparative Example 1, with the exception that 2,6-difluoro benzaldehyde (570 mg, 4.01 mmol) was used.

$^1$H NMR(200 MHz, CDCl$_3$) δ 8.26(s, 1H), 7.73(d, 1H, J=8.6 Hz), 7.57~7.46(m, 1H), 7.20~7.11(m, 1H), 4.06(s, 3H)

MS(m/z)M$^+$=210 (M$^+$)

PREPARATIVE EXAMPLE 34

Preparation of 4-Iodobenzothiophene-2-Carboxylic Acid Methyl Ester (Step 1) Preparation of 2-Fluoro-6-Iodo Benzaldehyde The title compound was prepared as a yellow liquid (2.0 g, 7.99 mmol, 89%) in the same manner as in Step 1 of Preparative Example 1, with the exception that 3-iodo fluorobenzene (2.0 g, 9.01 mmol) was used.

$^1$H NMR(200 MHz, CDCl$_3$) δ 10.15(s, 1H), 7.83~7.79(m, 1H), 7.28~7.12(m, 2H)

(Step 2) Preparation of 4-Iodobenzothiophene-2-Carboxylic Acid Methyl Ester

The title compound was prepared as a white solid (1.15 g, 3.61 mmol, 90%) in the same manner as in Step 2 of Preparative Example 1, with the exception that 2-fluoro-6-iodo benzaldehyde (1.0 g, 3.99 mmol), prepared in Step 1 of the present preparative example, was used.

$^1$H NMR(200 MHz, CDCl$_3$) δ 8.11(s, 1H), 7.84~7.80(m, 2H), 7.14(dd, 1H, J=7.4, 7.4 Hz), 3.96(s, 3H)

MS(m/z)M$^+$=318 (M$^+$)

PREPARATIVE EXAMPLE 35

Preparation of 4-Methylbenzothiophene-2-Carboxylic Acid Methyl Ester

4-Bromobenzothiophene-2-carboxylic acid methyl ester (200 mg, 0.74 mmol), obtained in Preparative Example 1, Pd(PPh$_3$)$_4$ (85 mg, 10 mmol %), and potassium carbonate (306 mg, 2.21 mmol) were dissolved in DMF (3 ml). After the addition of trimethylboroxine (0.12 ml, 0.89 mmol), the reaction solution was heated to reflux with stirring for 16 hours, then was extracted two times with ethyl acetate, washed with brine, dried over MgSO$_4$, and then filtered. The filtrate was concentrated under reduced pressure, and the residue was purified by silica gel column chromatography (hexane→hexane:ethyl acetate=60:1), thus obtaining the title compound as a pale yellow solid (140 mg, 0.68 mmol, 92%).

$^1$H NMR(200 MHz, CDCl$_3$) δ 8.15(s, 1H), 7.69(d, 1H, J=8.2 Hz), 7.35(dd, 1H, J=7.2, 8.2 Hz), 7.17(d, 1H, J=7.2 Hz), 3.95(s, 3H), 2.63(s, 3H)

MS(m/z)M$^+$206 (M$^+$)

PREPARATIVE EXAMPLE 36

Preparation of 4-Vinylbenzothiophene-2-Carboxylic Acid Methyl Ester

4-Bromobenzothiophene-2-carboxylic acid methyl ester (500 mg, 1.84 mmol), obtained in Preparative Example 1, and Pd(PPh$_3$)$_4$ (170 mg, 8 mmol %) were dissolved in toluene. (8 ml). After tributyl(vinyl)tin (0.81 ml, 2.76 mmol) was added, the reaction mixture was heated to reflux with stirring for 16 hours, then was extracted two times with ethyl acetate, washed with brine, dried over MgSO$_4$, and then filtered. The filtrate was concentrated under reduced pressure, and the residue was purified by silica gel column chromatography (hexane:ethyl acetate=60:1), thus obtaining the title compound as a pale yellow solid (247 mg, 1.13 mmol, 61%).

$^1$H NMR(200 MHz, CDCl$_3$) δ 8.29(s, 1H), 7.77(d, 1H, J=8.0 Hz), 7.57~7.40(m, 2H), 7.29~7.14(m, 1H), 5.84(d, 1H, J=17.6 Hz), 5.46(d, 1H, J=11.0 Hz), 3.95(s, 3H)

MS(m/z)M$^+$=218 (M$^+$)

PREPARATIVE EXAMPLE 37

Preparation of 4-Ethylbenzothiophene-2-Carboxylic Acid Methyl Ester

4-Vinylbenzothiophene-2-carboxylic acid methyl ester (150 mg, 0.69 mmol), obtained in Preparative Example 36, was dissolved in methanol (7 ml), and the reaction solution was hydrogenated with 50% Raney Ni (75 mg) under hydrogen gas of 40 psi at room temperature for 16 hours. After the termination of the reaction, the resulting reaction solution was filtered in order to remove the Ni component and then concentrated under reduced pressure. The residue was purified by silica gel column chromatography (hexane:ethyl acetate=20:1), thus obtaining the title compound as a pale yellow oil (110 mg, 0.50 mmol, 72%).

$^1$H NMR(200 MHz, CDCl$_3$) δ 8.19(s, 1H), 7.69(d, 1H, J=8 Hz), 7.39(dd, 1H, J=7.0, 8.2 Hz), 7.21(d, 1H, J=6.8 Hz), 3.95(s, 3H), 2.99(q, 2H), 1.35(t, 3H)

MS(m/z)M$^+$=220 (M$^+$)

PREPARATIVE EXAMPLE 38

Preparation of 4-Isopropylbenzothiophene-2-Carboxylic Acid Methyl Ester

ZnCl$_2$ (428 mg, 3.14 mmol), dried at a high temperature in a vacuum, was dissolved in THF (5 ml), and then a solution of 2M isopropylmagnesium chloride (1.6 ml, 3.2 mmol) in THF was slowly added dropwise. The reaction solution was stirred at 50° C. for 3 hours to provide zinc slurry.

4-Iodobenzothiophene-2-carboxylic acid methyl ester (500 mg, 1.57 mmol), obtained in Preparation Example 34, CuI (36 mg, 0.19 mmol), and Pd(dppf)Cl$_2$.CH$_2$Cl$_2$ (128 mg, 10 mmol %) were dissolved in THF (5 ml). After the slow addition of the zinc slurry, the reaction solution was stirred at room temperature for 16 hours, and then was extracted two times with ethyl acetate, washed with an aqueous solution of 1M hydrochloric acid, a saturated aqueous solution of sodium bicarbonate, and brine, dried over MgSO$_4$, and then filtered. The filtrate was concentrated under reduced pressure, and the residue was purified by silica gel column chromatography (hexane:ethyl acetate=60:1), thus obtaining the title compound as a pale yellow oil (254 mg, 1.08 mmol, 69%).

$^1$H NMR(200 MHz, CDCl$_3$) δ 8.24(s, 1H), 7.71~7.26(m, 3H), 3.95(s, 3H), 3.50(m, 1H), 1.38(d, 6H)

MS(m/z)M$^+$=234 (M$^+$)

PREPARATIVE EXAMPLE 39

Preparation of 4-Nitrobenzothiophene-2-Carboxylic Acid Methyl Ester

The title compound was prepared as a yellow solid (323 mg, 1.36 mmol, 53%) in the same manner as in Step 2 of Preparative Example 1, with the exception that 2,6-dinitro benzaldehyde (500 mg, 2.55 mmol) was used.

$^1$H NMR(200 MHz, CDCl$_3$) δ 8.88(s, 1H), 8.39(d, 1H, J=8.0 Hz), 8.18(d, 1H, J=8.2 Hz), 7.61(dd, 1H, J=8.0, 8.0 Hz), 4.00(s, 3H)

MS(m/z)M$^+$=237 (M$^+$)

PREPARATIVE EXAMPLE 40

Preparation of 4-Aminobenzothiophene-2-Carboxylic Acid Methyl Ester

The title compound was prepared as a yellow solid (159 mg, 0.77 mmol, 98%) in the same manner as in Preparative Example 37, with the exception that 4-nitrobenzothiophene-2-carboxylic acid methyl ester (185 mg, 0.7.8 mmol), obtained in Preparative Example 39, was used.

$^1$H NMR(200 MHz, CDCl$_3$) δ 8.44(s, 1H), 7.22~7.06(m, 2H), 6.53(d, 1H, J=7.6 Hz), 6.02(s, 2H), 3.85(s, 3H)

MS(m/z)M$^+$=207 (M$^+$)

PREPARATIVE EXAMPLE 41

Preparation of 4-Methoxybenzothiophene-2-Carboxylic Acid Methyl Ester (Step 1) Preparation of 2-Fluoro-6-Methoxy Benzaldehyde The solution of 3-Fluoro anisole (2.2 g, 17.44 mmol) in anhydrous THF (40 ml) under a nitrogen atmosphere was cooled to −78° C., and then n-BuLi (1.6 M, 19.18 mmol) was slowly added thereto. The reaction mixture was stirred at −78° C. for 1 hour, slowly added with DMF (1.6 ml, 20.93 mmol), and then stirred for 1 hour. After the termination of the reaction, the resulting reaction solution was added with dilute H$_2$SO$_4$, extracted two times with ethyl acetate, washed with brine, dried over MgSO$_4$, and then filtered. The filtrate was concentrated under reduced pressure, and the residue was purified by silica gel column chromatography (hexane:ethyl acetate=6:1), thus obtaining the title compound as a white solid (1.48 g, 9.6 mmol, 55%).

$^1$H NMR(200 MHz, CDCl$_3$) δ 10.43(s, 1H), 7.54~7.43(m, 1H), 6.79~6.68(m, 2H), 3.93(s, 3H)

(Step 2) Preparation of 4-Methoxybenzothiopene-2-Carboxylic Acid Methyl Ester

The title compound was prepared as a white solid (345 mg, 1.55 mmol, 48%) in the same manner as in Step 2 of Preparative Example 1, with the exception that 2-fluoro-6-methoxy benzaldehyde (500 mg, 3.24 mmol), obtained in Step 1 of the present preparative example, was used.

$^1$H NMR(200 MHz, CDCl$_3$) δ 8.23(s, 1H), 7.44~7.34(m, 2H), 6.77~6.73(m, 1H), 3.96(s, 3H), 3.93(s, 3H)

MS(m/z)M$^+$=222 (M$^+$)

PREPARATIVE EXAMPLE 42

Preparation of 4-Cyanobenzothiophene-2-Carboxylic Acid Methyl Ester

4-Bromobenzothiophene-2-carboxylic acid methyl ester (2.0 g, 7.38 mmol), obtained in Preparative Example 1, was dissolved in DMF (8 ml) and then allowed to react with CuCN at 200° C. for 20 min using a microwave creator. After the termination of the reaction, the resulting reaction solution was acidified with 8N hydrochloric acid, extracted three times with ethyl acetate, washed with brine, dried over anhydrous $MgSO_4$, and then filtered. The filtrate was concentrated under reduced pressure, and the residue was purified by silica gel column chromatography (hexane:ethyl acetate=20:1), thus obtaining the title compound as a white solid (1.28 g, 5.89 mmol, 80%).

$^1$H NMR(200 MHz, $CDCl_3$) δ 8.27(s, 1H), 8.10(d, 1H, J=8.0 Hz), 7.78(d, 1H, J=7.6 Hz), 7.56(dd, 1H, J=7.6, 8.0 Hz), 3.98(s, 3H)

MS(m/z)M$^+$=217 (M$^+$)

PREPARATIVE EXAMPLE 43

Preparation of Benzothiophene-2-Carboxylic Acid Methyl Ester

The title compound was prepared as a yellow solid (567 mg, 2.95 mmol, 73%) in the same manner as in Step 2 of Preparative Example 1, with the exception that 2-fluoro benzaldehyde (500 mg, 4.03 mmol) was used.

$^1$H NMR(200 MHz, $CDCl_3$) δ 8.06(s, 1H), 7.90~7.84(m, 2H), 7.50~7.36(m, 2H), 3.94(s, 3H)

MS(m/z)M$^+$=192 (M$^+$)

PREPARATIVE EXAMPLE 44

Preparation of 4-Bromo-5-Methylbenzothiophene-2-Carboxylic Acid Methyl Ester (Step 1) Preparation of 2-Bromo-3-Methyl-6-Fluoro Benzaldehyde The title compound was prepared as a pale yellow solid (1.1 g, 5.07 mmol, 96%) in the same manner as in Step 1 of Preparative Example 1, with the exception that 2-bromo-4-fluoro toluene (1.0 g, 5.29 mmol) was used.

$^1$H NMR(200 MHz, $CDCl_3$) δ 10.39(s, 1H), 7.45~7.38(m, 1H), 7.09~6.99(m, 1H), 2.43(s, 3H)

(Step 2) Preparation of 4-Bromo-5-Methylbenzothiophene-2-Carboxylic Acid Methyl Ester The title compound was prepared as a white solid (1.0 g, 3.51 mmol, 69%) in the same manner as in Step 2 of Preparative Example 1, with the exception that 2-bromo-3-methyl-6-fluoro benzaldehyde (1.1 g, 5.07 mmol), prepared in Step 1 of the present preparative example, was used.

$^1$H NMR(200 MHz, $CDCl_3$) δ 8.19(s, 1H), 7.67(d, 1H, J=8.4 Hz), 7.32(d, 1H, J=8.2 Hz), 3.95(s, 3H), 2.53(s, 3H)

MS(m/z)M$^+$=284 (M$^+$)

PREPARATIVE EXAMPLE 45

Preparation of 4-Chloro-5-Methylbenzothiophene-2-Carboxylic Acid Methyl Ester (Step 1) Preparation of 2-Chloro-3-Methyl-6-Fluoro Benzaldehyde The title compound was prepared as a pale yellow solid (1.13 g, 6.55 mmol, 95%) in the same manner as in Step 1 of Preparative Example 1, with the exception that 2-chloro-4-fluoro toluene (1.0 g, 6.92 mmol) was used.

$^1$H NMR(200 MHz, $CDCl_3$) δ 10.49(s, 1H), 7.46~7.39(m, 1H), 7.05~6.96(m, 1H), 2.39(s, 3H)

(Step 2) Preparation of 4-Chloro-5-Methylbenzothiophene-2-Carboxylic Acid Methyl Ester The title compound was prepared as a pale yellow solid (1.03 g, 4.28 mmol, 66%) in the same manner as in Step 2 of Preparative Example 1, with the exception that 2-chloro-3-methyl-6-fluoro benzaldehyde (1.12 g, 6.49 mmol), prepared in Step 1 of the present preparative example, was used.

$^1$H NMR(200 MHz, $CDCl_3$) δ 8.20(s, 1H), 7.64(d, 1H, J=8.2 Hz), 7.32(d, 1H, J=8.4 Hz), 3.95(s, 3H), 2.50(s, 3H)

MS(m/z)M$^+$=240 (M$^+$)

PREPARATIVE EXAMPLE 46

Preparation of 4,5-Dimethylbenzothiophene-2-Carboxylic Acid Methyl Ester

4-Bromo-5-methylbenzothiophene-2-carboxylic acid methyl ester (300 mg, 1.05 mmol), obtained in Preparative Example 44, Pd(PPh$_3$)$_4$ (49 mg, 4 mmol %), and methyl boronic acid (94 mg, 1.58 mmol) were dissolved in toluene (5 ml), following the addition of 2M potassium carbonate (1 ml, 2.1 mmol). The reaction solution was heated at reflux with stirring for 16 hours, and then was extracted two times with ethyl acetate, washed with brine, dried over $MgSO_4$, and then filtered. The filtrate was concentrated under reduced pressure, and the residue was purified by silica gel column chromatography (hexane:ethyl acetate=40:1), thus obtaining the title compound as a white solid (195 mg, 0.89 mmol, 84%).

$^1$H NMR(200 MHz, $CDCl_3$) δ 8.15(s, 1H), 7.58(d, 1H, J=8.2 Hz), 7.25(d, 1H, J=8.2 Hz), 3.94(s, 3H), 2.52(s, 3H), 2.38(s, 3H)

MS(m/z)M$^+$=220 (M$^+$)

PREPARATIVE EXAMPLE 47

Preparation of 4-Cyano-5-Methylbenzothiophene-2-Carboxylic Acid Methyl Ester

The title compound was prepared as a white solid (107 mg, 0.46 mmol, 52%) in the same manner as in Preparative Example 42, with the exception that 4-bromo-5-methylbenzothiophene-2-carboxylic acid methyl ester (255 mg, 0.89 mmol), obtained in Preparative Example 44, was used.

$^1$H NMR(200 MHz, $CDCl_3$) δ 8.23(s, 1H), 7.95(d, 1H, J=8.4 Hz), 7.39(d, 1H, J=8.4 Hz), 3.98(s, 3H), 2.69(s, 3H)

MS(m/z)M$^+$=231 (M$^+$)

PREPARATIVE EXAMPLE 48

Preparation of 4-Bromo-6-Methylbenzothiophene-2-Carboxylic Acid Methyl Ester (Step 1) Preparation of 2,6-Dibromo-4-Methyl Benzaldehyde The title compound was prepared as a white solid (662 mg, 2.38 mmol, 60%) in the same manner as in Step 1 of Preparative Example 1, with the exception that 3,5-dibromo toluene (1.0 g, 4.0 mmol) was used.

$^1$H NMR(200 MHz, $CDCl_3$) δ 10.24(s, 1H), 7.47(s, 2H), 2.37(s, 3H)

(Step 2) Preparation of
4-Bromo-6-Methylbenzothiophene-2-Carboxylic
Acid Methyl Ester The title compound was prepared as a white solid (557 mg, 1.95 mmol, 82%) in the same manner as in Step 2 of Preparative Example 1, with the exception that 2,6-dibromo-4-methyl benzaldehyde (660 mg, 2.37 mmol), prepared in Step 1 of the present preparative example, was used.
$^1$H NMR(200 MHz, CDCl$_3$) δ 8.12(s, 1H), 7.57(s, 1H), 7.42(s, 1H), 3.95(s, 3H), 2.46(s, 3H)
MS(m/z)M$^+$=284 (M$^+$)

PREPARATIVE EXAMPLE 49

Preparation of
4,6-Dimethylbenzothiophene-2-Carboxylic Acid
Methyl Ester

The title compound was prepared as a white solid (158 mg, 0.72 mmol, 93%) in the same manner as in Preparative Example 46, with the exception that 4-bromo-6-methylbenzothiophene-2-carboxylic acid methyl ester (220 mg, 0.77 mmol), obtained in Preparative Example 48, was used.
$^1$H NMR(200 MHz, CDCl$_3$) δ 8.12(s, 1H), 7.50(s, 1H), 7.04(s, 1H), 3.96(s, 3H), 2.61(s, 3H), 2.46(s, 3H)
MS(m/z)M$^+$=220 (M$^+$)

PREPARATIVE EXAMPLE 50

Preparation of
4-Cyano-6-Methylbenzothiophene-2-Carboxylic
Acid Methyl Ester

The title compound was prepared as a white solid (135 mg, 0.58 mmol, 64%) in the same manner as in Preparative Example 42, with the exception that 4-bromo-6-methylbenzothiophene-2-carboxylic acid methyl ester (260 mg, 0.91 mmol), obtained in Preparative Example 48, was used.
$^1$H NMR(200 MHz, CDCl$_3$) δ 8.22(s, 1H), 7.88(s, 1H), 7.59(s, 1H), 3.97(s, 3H), 2.53(s, 3H)
MS(m/z)M$^+$=231 (M$^+$)

EXAMPLE 1

Preparation of
(4-Bromobenzothiophene-2-Carbonyl)Guanidine
Methanesulfonate

The compound (88 mg, 0.32 mmol) obtained in Preparative Example 1 was dissolved in DMF (3 ml). The reaction solution was added with a 2M guanidine methanol solution (1 ml, 2.0 mmol) and then allowed to react at room temperature for 3 hours. After the termination of the reaction via the addition of water, the resulting reaction solution was extracted two times with ethyl acetate, washed with brine, dried over MgSO$_4$, and then filtered. The filtrate was concentrated under reduced pressure, and the obtained residue was dissolved in acetone. 2~3 Drops of methanesulfonic acid were added, and thus the title compound was deposited as a solid. The produced solid was filtered, and subsequently washed with ether, thereby yielding the title compound as a yellow solid (73 mg, 0.18 mmol, 57%).
$^1$H NMR(300 MHz, DMSO) δ 11.70(br s, 1H), 8.40(s, 1H), 8.31(br, 4H), 8.16(d, 1H, J=8.1 Hz), 7.78(d, 1H, J=7.8 Hz), 7.51(dd, 1H, J=7.8, 7.8 Hz), 2.37.(s, 3H)
MS (m/z)M$^+$=299 (M$^+$)

EXAMPLE 2

Preparation of [4-(2-Chlorophenyl)Benzothiophene-
2-Carbonyl]Guanidine Methanesulfonate The title compound was prepared as a white solid (125 mg, 0.29 mmol, 4.5%) in the same manner as in Example 1, with the exception that the compound (200 mg, 0.66 mmol) obtained in Preparative Example 2 was used.
$^1$H NMR(300 MHz, CD$_3$OD) δ 7.86(d, 1H, J=8.4 Hz), 7.69(s, 1H), 7.48~7.19(m, 6H), 2.49(s, 3H)
MS(m/z)M$^+$=329 (M$^+$)

EXAMPLE 3

Preparation of [4-(3-Chlorophenyl)Benzothiophene-
2-Carbonyl]Guanidine Methanesulfonate The title compound was prepared as a white solid (85 mg, 0.20 mmol, 64%) in the same manner as in Example 1, with the exception that the compound (95 mg, 0.31 mmol) obtained in Preparative Example 3 was used.
$^1$H NMR(30 0 MHz, CD$_3$OD) δ 8.37(s, 1H), 8.19(d, 1H, J=8.1 Hz), 7.83~7.62(m, 6H), 2.84(s, 3H)
MS(m/z)M$^+$=329 (M$^+$)

EXAMPLE 4

Preparation of [4-(4-Chlorophenyl)Benzothiophene-
2-Carbonyl]Guanidine Methanesulfonate The title compound was prepared as a white solid (110 mg, 0.26 mmol, 39%) in the same manner as in Example 1, with the exception that the compound (200 mg, 0.66 mmol) obtained in Preparative Example 4 was used.
$^1$H NMR(300 MHz, DMSO) δ 11.61(br s, 1H), 8.31(s, 1H), 8.25(br s, 4H), 8.16(d, 1H, J=8.1 Hz), 7.69~7.46(m, 6H), 2.33(s, 3H)
MS(m/z)M$^+$=329 (M$^+$)

EXAMPLE 5

Preparation of [4-(2-Fluorophenyl)Benzothiophene-
2-Carbonyl]Guanidine Methanesulfonate The title compound was prepared as a white solid (144 mg, 0.35 mmol, 54%) in the same manner as in Example 1, with the exception that the compound (185 mg, 0.65 mmol) obtained in Preparative Example 5 was used.
$^1$H NMR(300 MHz, DMSO) δ 11.51(br s, 1H), 8.25(br, 4H), 8.19(d, 1H, J=8.1 Hz), 8.09(s, 1H), 7.71~7.39(m, 6H), 2.31(s, 3H)
MS(m/z)M$^+$=313 (M$^+$)

EXAMPLE 6

Preparation of [4-(3-Fluorophenyl)Benzothiophene-
2-Carbonyl]Guanidine Methanesulfonate The title compound was prepared as a white solid (63 mg, 0.15 mmol, 58%) in the same manner as in Example 1, with the exception that the compound (76 mg, 0.27 mmol) obtained in Preparative Example 6 was used.
 $^1$H NMR(300 MHz, CD$_3$OD) δ 8.28(s, 1H), 8.05(d, 1H, J=8.4 Hz), 7.69~7.26(m, 6H), 2.71(s, 3H)
 MS(m/z)M$^+$=313 (M$^+$)

EXAMPLE 7

Preparation of [4-(4-Fluorophenyl)Benzothiophene-2-Carbonyl]Guanidine Methanesulfonate The title compound was prepared as a white solid (115 mg, 0.28 mmol, 68%) in the same manner as in Example 1, with the exception that the compound (118 mg, 0.41 mmol) obtained in Preparative Example 7 was used.
 $^1$H NMR(300 MHz, DMSO) δ 11.56(br s, 1H), 8.35(br s, 4H), 8.34(s, 1H), 8.15(d, 1H, J=8.1 Hz), 7.70~7.40(m, 6H), 2.35(s, 3H)
 MS(m/z)M$^+$=313 (M$^+$)

EXAMPLE 8

Preparation of [4-(2-Methylphenyl)Benzothiophene-2-Carbonyl]Guanidine Methanesulfonate The title compound was prepared as a white solid (170 mg, 0.42 mmol, 67%) in the same manner as in Example 1, with the exception that the compound (178 mg, 0.63 mmol) obtained in Preparative Example 8 was used.
 $^1$H NMR(300 MHz, DMSO) δ 11.42(br s, 1H), 8.20(br s, 4H), 8.14(d, 1H, J=8.4 Hz), 7.88(s, 1H), 7.65(dd, 1H, J=7.8, 7.8 Hz), 7.43~7.27(m, 5H), 2.30(s, 3H), 2.08(s, 3H)
 MS(m/z)M$^+$=309 (M$^+$)

EXAMPLE 9

Preparation of [4-(3-Methylphenyl)Benzothiophene-2-Carbonyl]Guanidine Methanesulfonate The title compound was prepared as a white solid (93 mg, 0.23 mmol, 51%) in the same manner as in Example 1, with the exception that the compound (127 mg, 0.45 mmol) obtained in Preparative Example 9 was used.
 $^1$H NMR(300 MHz, DMSO) δ 11.49(br s, 1H), 8.33(s, 1H), 8.23(br s, 4H), 8.12(d, 1H, J=8.1 Hz), 7.65(dd, 1H, J=7.2, 7.8 Hz), 7.48~7.32(m, 5H), 2.43(s, 3H), 2.29(s, 3H)
 MS(m/z)M$^+$=309 (M$^+$)

EXAMPLE 10

Preparation of [4-(4-Methylphenyl)Benzothiophene-2-Carbonyl]Guanidine Methanesulfonate The title compound was prepared as a white solid (110 mg, 0.27 mmol, 49%) in the same manner as in Example 1, with the exception that the compound (155 mg, 0.55 mmol) obtained in Preparative Example 10 was used.
 $^1$H NMR(300 MHz, DMSO) δ 11.47(br s, 1H), 8.32~8.09 (m, 6H), 7.64~7.20(m, 6H), 2.42(s, 3H), 2.31(s, 3H)
 MS(m/z)M$^+$=309 (M$^+$)

EXAMPLE 11

Preparation of [4-(2-Methoxyphenyl)Benzothiophene-2-Carbonyl]Guanidine Methanesulfonate The title compound was prepared as a white solid (110 mg, 0.26 mmol, 45%) in the same manner as in Example 1, with the exception that the compound (172 mg, 0.58 mmol) obtained in Preparative Example 11 was used.
 $^1$H NMR(300 MHz, DMSO) δ 11.47(br s, 1H), 8.22(br s, 4H), 8.09(d, 1H, J=7.5 Hz), 7.99(s, 1H), 7.62(m, 1H), 7.50 (dd, 1H, J=7.8, 8.4 Hz), 7.39~7.32(m, 2H), 7.25(d, 1H, J=7.8 Hz), 7.13(dd, 1H, J=7.2, 7.2 Hz), 3.73(s, 3H), 2.30(s, 3H)
 MS(m/z)M$^+$=325 (M$^+$)

EXAMPLE 12

Preparation of [4-(3-Methoxyphenyl)Benzothiophene-2-Carbonyl]Guanidine Methanesulfonate The title compound was prepared as a pale yellow solid (65 mg, 0.15 mmol, 49%) in the same manner as in Example 1, with the exception that the compound (95 mg, 0.32mmol) obtained in Preparative Example 12 was used.
 $^1$H NMR(300 MHz, DMSO) δ 11.39(br s, 1H), 8.24(s, 1H), 8.12(br s, 4H), 7.99(d, 1H, J=8.1 Hz), 7.52(dd, 1H, J=7.5, 8.1 Hz), 7.39~7.35(m, 2H), 7.05~6.94(m, 3H), 3.71(s, 3H), 2.18 (s, 3H)
 MS(m/z)M$^+$=325 (M$^+$)

EXAMPLE 13

Preparation of [4-(4-Methoxyphenyl)Benzothiophene-2-Carbonyl]Guanidine Methanesulfonate The title compound was prepared as a white solid (131 mg, 0.31 mmol, 77%) in the same manner as in Example 1, with the exception that the compound (120 mg, 0.40 mmol) obtained in Preparative Example 13 was used.
 $^1$H NMR(300 MHz, DMSO) δ 11.48(br s, 1H), 8.35(s, 1H), 8.27(br s, 4H), 8.09(d, 1H, J=8.1 Hz), 7.64(dd, 1H, J=7.8, 8.1 Hz), 7.56(d, 2H, J=8.4 Hz), 7.45(d, 1H, J=7.5 Hz), 7.15(d, 2H, J=8.4 Hz), 3.86(s, 3H), 2.31(s, 3H)
 MS(m/z)M$^+$=325 (M$^+$)

EXAMPLE 14

Preparation of [4-(2-Trifluoromethylphenyl)Benzothiophene-2-Carbonyl]Guanidine Methanesulfonate The title compound was prepared as a white solid (77 mg, 0.17 mmol, 47%) in the same manner as in Example 1, with the exception that the compound (120 mg, 0.36 mmol) obtained in Preparative Example 14 was used.
 $^1$H NMR(300 MHz, DMSO) δ 11.34(br s, 1H), 8.22(br s, 4H), 8.19(d, 1H, J=7.2 Hz), 7.97(d, 1H, J=7.8 Hz), 7.87~7.64 (m, 4H), 7.53(d, 1H, J=7.8 Hz), 7.36(d, 1H, J=6.3 Hz), 2.30(s, 3H)
 MS(m/z)M$^+$=363 (M$^+$)

EXAMPLE 15

Preparation of [4-(3-Trifluoromethylphenyl)Benzothiophene-2-Carbonyl]Guanidine Methanesulfonate The title compound was prepared as a white solid (228 mg, 0.50 mmol, 56%) in the same manner as in Example 1, with the exception that the compound (200 mg, 0.89 mmol) obtained in Preparative Example 15 was used.

¹H NMR(300 MHz, CD₃OD) δ 8.20(s, 1H), 8.08(d, 1H, J=8.1 Hz), 7.91~7.80(m, 4H), 7.69(dd, 1H, J=7.5, 7.5 Hz), 7.53(d, 1H, J=7.2 Hz), 2.68(s, 3H)

MS(m/z)M⁺=363 (M⁺)

EXAMPLE 16

Preparation of [4-(4-Trifluoromethylphenyl)Benzothiophene-2-Carbonyl]Guanidine Methanesulfonate The title compound was prepared as a white solid (130 mg, 0.28 mmol, 63%) in the same manner as in Example 1, with the exception that the compound (150 mg, 0.45 mmol) obtained in Preparative Example 16 was used.

¹H NMR(300 MHz, DMSO) δ 11.51(br s, 1H), 8.32(s, 1H), 8.28(br s, 4H), 8.21(d, 1H, J=8.4 Hz), 7.97~7.85(m, 4H), 7.71(dd, 1H, J=7.5, 8.1 Hz), 7.57(d, 1H, J=7.2 Hz), 2.31(s, 3H)

MS(m/z)M⁺=363 (M⁺)

EXAMPLE 17

Preparation of (4-Phenylbenzothiophene-2-Carbonyl)Guanidine Methanesulfonate

The title compound was prepared as a white solid (105 mg, 0.27 mmol, 48%) in the same manner as in Example 1, with the exception that the compound (150 mg, 0.56 mmol) obtained in Preparative Example 17 was used.

¹H NMR(300 MHz, CD₃OD) δ 8.28(s, 1H), 7.99(d, 1H, J=8.1 Hz), 7.67~7.47(m, 7H), 2.68(s, 3H)

MS(m/z)M⁺=296 (M⁺)

EXAMPLE 18

Preparation of [4-(1-Naphthalenyl)Benzothiophene-2-Carbonyl]Guanidine Methanesulfonate The title compound was prepared as a white solid (100 mg, 0.23 mmol, 60%) in the same manner as in Example 1, with the exception that the compound (120 mg, 0.38 mmol) obtained in Preparative Example 18 was used.

¹H NMR(300 MHz, DMSO) δ 11.28(br s, 1H), 8.57(br s, 4H), 8.25(d, 1H, J=8.1 Hz), 8.09(dd, 1H, J=8.1, 8.1 Hz), 7.79~7.67(m, 4H), 7.58~7.43(m, 5H), 2.29(s, 3H)

MS(m/z)M⁺=345 (M⁺)

EXAMPLE 19

Preparation of [4-(3,5-Dichlorophenyl)Benzothiophene-2-Carbonyl]Guanidine Methanesulfonate The title compound was prepared as a white solid (80 mg, 0.17 mmol, 62%) in the same manner as in Example 1, with the exception that the compound (94 mg, 0.28 mol) obtained in Preparative Example 19 was used.

¹H NMR(300 MHz, DMSO) δ 11.52(br s, 1H), 8.24(br s, 4H), 8.25(s, 1H), 8.21(d, 1H, J=8.1 Hz), 7.79~7.50(m, 5H), 2.32(s, 3H)

MS(m/z)M⁺=363 (M⁺)

EXAMPLE 20

Preparation of [4-(2,5-Dichlorophenyl)Benzothiophene-2-Carbonyl]Guanidine

The title compound was prepared as a white solid (130 mg, 0.36 mmol, 73%) in the same manner as in Example 1, with the exception that the compound (164 mg, 0.49 mmol) obtained in Preparative Example 20 was used, and yielded as a free form but not as a methanesulfonate salt. The residue was purified by silica gel column chromatography (MeOH:CH₂Cl₂=1:10).

¹H NMR(300 MHz, DMSO) δ 8.02(d, 1H, J=7.9 Hz), 7.69(d, 1H, J=8.3 Hz), 7.62~7.57(m, 2H), 7.51(dd, 1H, J=7.5, 7.9 Hz), 7.37(s, 1H), 7.32( d, 1H, J=7.2 Hz)

MS(m/z)M⁺=363 (M⁺)

EXAMPLE 21

Preparation of [4-(2,3-Dichlorophenyl)Benzothiophene-2-Carbonyl]Guanidine Methanesulfonate The title compound was prepared as a white solid (130 mg, 0.28 mmol, 48%) in the same manner as in Example 1, with the exception that the compound (200 mg, 0.59 mmol) obtained in Preparative Example 21 was used.

¹H NMR(300 MHz, DMSO) δ 11.42(br s, 1H), 8.32(br s, 4H), 8.22(d, 1H, J=7.8 Hz), 7.89(s, 1H), 7.82(d, 1H, J=7.8 Hz), 7.66(dd, 1H, J=7.8, 7.8 Hz), 7.59~7.43(m, 3H), 2.31(s, 3H)

MS(m/z)M⁺=363 (M⁺)

EXAMPLE 22

Preparation of [4-(2-Methoxy-5-Chlorophenyl)Benzothiophene-2-Carbonyl]Guanidine Methanesulfonate The title compound was prepared as a white solid (125 mg, 0.27 mmol, 46%) in the same manner as in Example 1, with the exception that the compound.(200 mg, 0.6.0 mmol) obtained in Preparative Example 22 was used.

¹H NMR(300 MHz, CD₃OD) δ 7.92(d, 1H), 7.81(s, 1H), 7.54(dd, 1H), 7.41~7.23(m, 3H), 7.12(d, 1H), 3.67(s, 3H), 2.60(s, 3H)

MS(m/z)M⁺=360 (M⁺)

EXAMPLE 23

Preparation of [4-(3-Chloro-4-Fluorophenyl)Benzothiophene-2-Carbonyl]Guanidine Methanesulfonate The title compound was prepared as a white solid (110 mg, 0.25 mmol, 50%) in the same manner as in Example 1, with the exception that the compound (160 mg, 0.50 mmol) obtained in Preparative Example 23 was used.

¹H NMR(300 MHz, DMSO) δ 11.53(br s, 1H), 8.30(br s, 4H), 8.29(s, 1H), 8.18(d, 1H, J=8.4 Hz), 7.85(d, 1H, J=7.5 Hz), 7.70~7.53(m, 3H), 7.52(d, 1H, J=7.2 Hz), 2.32(s, 3H)

MS(m/z)M⁺=347 (M⁺)

EXAMPLE 24

Preparation of [4-(3,5-Difluorophenyl)Benzothiophene-2-Carbonyl]Guanidine Methanesulfonate The title compound was prepared as a white solid (160 mg, 0.37 mmol, 71%) in the same manner as in Example 1, with the exception that the compound (160 mg, 0.53 mmol) obtained in Preparative Example 24 was used.

$^1$H NMR(300 MHz, DMSO) δ 11.52(br s, 1H), 8.34(s, 1H), 8.32(br s, 4H), 8.21(d, 1H, J=8.1 Hz), 7.68(dd, 1H, J=7.5, 8.1 Hz), 7.56(d, 1H, J=7.2 Hz), 7.45~7.38(m, 3H), 2.32(s, 3H)
MS(m/z)M$^+$=331 (M$^+$)

EXAMPLE 25

Preparation of [4-(2,5-Difluorophenyl)Benzothiophene-2-Carbonyl]Guanidine Methanesulfonate The title compound was prepared as a white solid (53 mg, 0.12 mmol, 29%) in the same manner as in Example 1, with the exception that the compound (132 mg, 0.43 mmol) obtained in Preparative Example 25 was used.

$^1$H NMR(300 MHz, DMSO) δ 11.47(br s, 1H), 8.23~8.09 (m, 6H), 7.69~7.66(m, 1H), 7.52~7.43(m, 4H), 2.30(s, 3H)
MS(m/z)M$^+$=331 (M$^+$)

EXAMPLE 26

Preparation of [4-(2,3-Difluorophenyl)Benzothiophene-2-Carbonyl]Guanidine Methanesulfonate The title compound was prepared as a white solid (148 mg, 0.35 mmol, 70%) in the same manner as in Example 1, with the exception that the compound (150 mg, 0.49 mmol) obtained in Preparative Example 26 was used.

$^1$H NMR(300 MHz, DMSO) δ 11.48(br s, 1H), 8.35(br s, 4H), 8.24(d, 1H, J=8.1 Hz), 8.11(s, 1H), 7.71(dd, 1H, J=7.5, 7.8 Hz), 7.64~7.58(m, 1H), 7.54(d, 1H, J=7.2 Hz), 7.45~7.37 (m, 2H), 2.31(s, 3H)
MS(m/z)M$^+$=331 (M$^+$)

EXAMPLE 27

Preparation of [4-(3,4-Difluorophenyl)Benzothiophene-2-Carbonyl]Guanidine Methanesulfonate The title compound was prepared as a white solid (147 mg, 0.34 mmol, 78%) in the same manner as in Example 1, with the exception that the compound (134 mg, 0.44 mmol) obtained in Preparative Example 27 was used.

$^1$H NMR(300 MHz, CD$_3$OD) δ 8.24(s, 1H), 8.05(d, 1H, J=8.2 Hz), 7.67~7.42(m, 5H), 2.69(s, 3H)
MS(m/z)M$^+$=331 (M$^+$)

EXAMPLE 28

Preparation of [4-(2-Methyl-5-Fluorophenyl)Benzothiophene-2-Carbonyl]Guanidine Methanesulfonate The title compound was prepared as a white solid (75 mg, 0.18 mmol, 38%) in the same manner as in Example 1, with the exception that the compound (140 mg, 0.47 mmol) obtained in Preparative Example 28 was used.

$^1$H NMR(300 MHz, DMSO) δ 11.41(br s, 1H), 8.35(br s, 4H), 8.16(d, 1H, J=7.2 Hz), 7.88(s, 1H), 7.65(dd, 1H, J=7.2, 8.4 Hz), 7.48~7.15(m, 4H), 2.31(s, 3H), 2.08(s, 3H)
MS(m/z)M$^+$=327 (M$^+$)

EXAMPLE 29

Preparation of [4-(2-Fluoro-5-Methylphenyl)Benzothiophene-2-Carbonyl]Guanidine Methanesulfonate The title compound was prepared as a white solid (142 mg, 0.34 mmol, 63%) in the same manner as in Example 1, with the exception that the compound (160 mg, 0.53 mmol) obtained in Preparative Example 29 was used.

$^1$H NMR(300 MHz, DMSO) δ 11.51(br s, 1H), 8.31(br s, 4H), 8.18(d, 1H, J=8.1 Hz), 8.09(s, 1H), 7.67(dd, 1H, J=7.8, 7.8 Hz), 7.48(d, 1H, J=7.2 Hz), 7.35~7.29(m, 3H), 2.39(s, 3H), 2.31(s, 3H)
MS(m/z)M$^+$=327 (M$^+$)

EXAMPLE 30

Preparation of [4-(3,5-Dimethylphenyl)Benzothiophene-2-Carbonyl]Guanidine Methanesulfonate The title compound was prepared as a white solid (95 mg, 0.23 mmol, 43%) in the same manner as in Example 1, with the exception that the compound (155 mg, 0.52 mmol) obtained in Preparative Example 30 was used.

$^1$H NMR(300 MHz, DMSO) δ 11.47(br s, 1H), 8.33(s, 1H), 8.20(br s, 4H), 8.12(d, 1H, J=8.1 Hz), 7.64(dd, 1H, J=6.9, 8.1 Hz), 7.45(d, 1H, J=7.5 Hz), 7.19~7.15(m, 3H), 2.39(s, 6H), 2.30(s, 3H)
MS(m/z)M$^+$=323 (M$^+$)

EXAMPLE 31

Preparation of [4-(2,5-Dimethylphenyl)Benzothiophene-2-Carbonyl]Guanidine Methanesulfonate The title compound was prepared as a white solid (136 mg, 0.32 mmol, 42%) in the same manner as in Example 1, with the exception that the compound (230 mg, 0.78 mmol) obtained in Preparative Example 31 was used.

$^1$H NMR(300 MHz, DMSO) δ 11.43(br s, 1H), 8.19(br s, 4H), 8.13(d, 1H, J=8.1 Hz), 7.89(s, 1H), 7.64(dd, 1H, J=7.8, 7.8 Hz), 7.33~7.29(m, 2H), 7.22(d, 1H, J=7.8 Hz), 7.09(s, 1H), 2.33(s, 3H), 2.31(s, 3H), 2.01(s, 3H)
MS(m/z)M$^+$=323 (M$^+$)

EXAMPLE 32

Preparation of (4-Chlorobenzothiophene-2-Carbonyl)Guanidine Methanesulfonate

The title compound was prepared as a white solid (110 mg, 0.31 mmol, 36%) in the same manner as in Example 1, with the exception that the compound (200 mg, 0.89 mmol) obtained in Preparative Example 32 was used.

¹H NMR(300 MHz, DMSO) δ 11.66(br s, 1H), 8.45(s, 1H), 8.40(br s, 4H), 8.13(d, 1H, J=7.8 Hz), 7.65~7.56(m, 2H), 2.34(s, 3H)

EXAMPLE 33

Preparation of (4-Fluorobenzothiophene-2-Carbonyl)Guanidine Methanesulfonate

The title compound was prepared as a white solid (158 mg, 0.47 mmol, 77%) in the same manner as in Example 1, with the exception that the compound (127 mg, 0.61 mmol) obtained in Preparative Example 33 was used.
¹H NMR(300 MHz, DMSO) δ 11.60(br s, 1H), 8.41(s, 1H), 8.26(br s, 4H), 7.99(d, 1H, J=8.1 Hz), 7.66~7.59(m, 1H), 7.35(dd, 1H, J=7.8, 8.1 Hz), 2.36(s, 3H)
MS(m/z)M⁺=237 (M⁺)

EXAMPLE 34

Preparation of (4-Iodobenzothiophene-2-Carbonyl)Guanidine Methanesulfonate

The title compound was prepared as a white solid (107 mg, 0.24 mmol, 39%) in the same manner as in Example 1, with the exception that the compound (200 mg, 0.63 mmol) obtained in Preparative Example 34 was used.
¹H NMR(300 MHz, DMSO) δ 11.70(br s, 1H), 8.32(s, 1H), 8.29(br s, 4H), 8.15(d, 1H, J=8.1 Hz), 7.96(d, 1H, J=7.5 Hz), 7.31(dd, 1H, J=7.8, 8.1 Hz), 2.35(s, 3H)
MS(m/z)M⁺=345 (M⁺)

EXAMPLE 35

Preparation of (4-Methylbenzothiophene-2-Carbonyl)Guanidine Methanesulfonate

The title compound was prepared as a white solid (43 mg, 0.13 mmol, 28%) in the same manner as in Example 1, with the exception that the compound (95 mg, 0.46 mmol) obtained in Preparative Example 35 was used.
¹H NMR(300 MHz, DMSO) δ 11.57(br s, 1H), 8.42(s, 1H), 8.29(br s, 4H), 7.93(d, 1H, J=8.4 Hz), 7.47(dd, 1H, J=7.5, 7.8 Hz), 7.32(d, 1H, J=7.2 Hz), 2.66(s, 3H), 2.35(s, 3H)
MS(m/z)M⁺=233 (M⁺)

EXAMPLE 36

Preparation of (4-Vinylbenzothiophene-2-Carbonyl)Guanidine Methanesulfonate

The title compound was prepared as a pale yellow solid (54 mg, 0.16 mmol, 44%) in the same manner as in Example 1, with the exception that the compound (78 mg, 0.36 mmol) obtained in Preparative Example 36 was used.
¹H NMR(300 MHz, DMSO) δ 11.69(br s, 1H), 8.72(s, 1H), 8.58(br s, 4H), 8.19(d, 1H, J=7.8 Hz), 7.86(d, 1H, J=7.2 Hz), 7.72(dd, 1H, J=7.5, 7.5 Hz), 7.44(dd, 1H, J=10.8, 11.1 Hz), 6.18(d, 1H, J=17.1 Hz), 5.72(d, 1H, J=11.1 Hz), 2.48(s, 3H)
MS(m/z)M⁺=245 (M⁺)

EXAMPLE 37

Preparation of (4-Ethylbenzothiophene-2-Carbonyl)Guanidine Methanesulfonate

The title compound was prepared as a white solid (108 mg, 0.31 mmol, 63%) in the same manner as in Example 1, with the exception that the compound (110 mg, 0.50 mmol) obtained in Preparative Example 37 was used.
¹H NMR(300 MHz, DMSO) δ 11.54(br s, 1H), 8.48(s, 1H), 8.33(br s, 4H), 7.93(d, 1H, J=8.1 Hz), 7.50(dd, 1H, J=7.5, 7.8 Hz), 7.33(d, 1H, J=7.2 Hz), 2.99(q, 2H), 2.36(s, 3H), 1.31(t, 3H)
MS(m/z)M⁺=247 (M⁺)

EXAMPLE 38

Preparation of (4-Isopropylbenzothiophene-2-Carbonyl)Guanidine Methanesulfonate

The title compound was prepared as a white solid (168 mg, 0.47 mmol, 46%) in the same manner as in Example 1, with the exception that the compound (240 mg, 1.02 mmol) obtained in Preparative Example 38 was used.
¹H NMR(300 MHz, CD₃OD) δ 8.49(s, 1H), 7.82(d, 1H, J=8.1 Hz), 7.53(dd, 1H, J=7.6, 7.9 Hz), 7.41(d, 1H, J=7.4 Hz), 3.58(m, 1H), 2.73(s, 3H), 1.43(d, 6H)
MS(m/z)M⁺=261 (M⁺)

EXAMPLE 39

Preparation of (4-Nitrobenzothiophene-2-Carbonyl)Guanidine Methanesulfonate

The title compound was prepared as a yellow solid (81 mg, 0.23 mol, 54%) in the same manner as in Example 1, with the exception that the compound (100 mg, 0.42 mmol) obtained in Preparative Example 39 was used.
¹H NMR(300 MHz, DMSO) δ 11.59(br s, 1H), 8.95(s, 1H), 8.64(d, 1H, J=8.1 Hz), 8.47(d, 1H, J=7.8 Hz), 8.27(br s, 4H), 7.82(dd, 1H, J=7.8, 8.1 Hz), 2.34(s, 3H)
MS(m/z)M⁺=264 (M⁺)

EXAMPLE 40

Preparation of (4-Aminobenzothiophene-2-Carbonyl)Guanidine Methanesulfonate

The title compound was prepared as a yellow solid (70 mg, 0.21 mmol, 38%) in the same manner as in Example 1, with the exception that the compound (115 mg, 0.56 mmol) obtained in Preparative Example 40 was used.
¹H NMR(300 MHz, DMSO) δ 11.41(br s, 1H), 8.48(s, 1H), 8.24(br s, 4H), 7.27~7.14(m, 2H), 6.59(d, 1H, J=7.8 Hz), 2.38(s, 3H)
MS(m/z)M⁺=234 (M⁺)

EXAMPLE 41

Preparation of
(4-Methoxybenzothiophene-2-Carbonyl)Guanidine
Methanesulfonate

The title compound was prepared as a white solid (145 mg, 0.42 mol, 50%) in the same manner as in Example 1, with the exception that the compound (188 mg, 0.85 mmol) obtained in Preparative Example 41 was used.

$^1$H NMR(300 MHz, DMSO) δ 11.44(br s, 1H), 8.42(s, 1H), 8.20(br s, 4H), 7.65(d, 1H, J=8.1 Hz), 7.55(dd, 1H, J=8.1, 8.1 Hz), 7.03(d, 1H, J=7.8 Hz), 3.99(s, 3H), 2.34(s, 3H)

MS (m/z)M$^+$=249 (M$^+$)

EXAMPLE 42

Preparation of
(4-Cyanobenzothiophene-2-Carbonyl)Guanidine
Methanesulfonate

The title compound was prepared as a white solid (2.4 g, 7.12 mmol, 88%) in the same manner as in Example 1, with the exception that the compound (1.76 g, 8.1 mmol) obtained in Preparative Example 42 was used.

$^1$H NMR(300 MHz, CD$_3$OD) δ 8.38(s, 1H), 8.31(d, 1H, J=8.3 Hz), 7.89(d, 1H, J=7.4 Hz), 7.64(dd, 1H, J=7.4, 8.2 Hz), 2.66(s, 3H)

MS(m/z)M$^+$=244 (M$^+$)

EXAMPLE 43

Preparation of (4-Trifluoromethylbenzothiophene-2-Carbonyl)Guanidine Methanesulfonate The title compound was prepared as a white solid (170 mg, 0.51 mmol, 77%) in the same manner as in Example 1, with the exception that trifluoromethylbenzothiophene-2-carbonyl methyl ester (138 mg, 0.67 mmol) was used.

$^1$H NMR(300 MHz, DMSO) δ 11.68(br s, 1H), 8.51(d, 1H, J=8.4 Hz), 8.47(s, 1H), 8.34(br s, 4H), 7.94(d, 1H, J=7.2 Hz), 7.75(dd, 1H, J=7.2, 8.4 Hz), 2.35(s, 3H)

MS(m/z)M$^+$=287 (M$^+$)

EXAMPLE 44

Preparation of
(Benzothiophene-2-Carbonyl)Guanidine
Methanesulfonate

The title compound was prepared as a white solid (113 mg, 0.36 mmol, 35%) in the same manner as in Example 1, with the exception that the compound (200 mg, 1.04 mmol) obtained in Preparative Example 43 was used.

$^1$H NMR(300 MHz, DMSO) δ 11.58(br s, 1H), 8.37(s, 1H), 8.28(br s, 4H), 8.14~8.09(m, 2H), 7.61~7.50(m, 2H), 2.39(s, 3H)

MS(m/z)M$^+$=218 (M$^+$)

EXAMPLE 45

Preparation of (4-Bromo-5-Methylbenzothiophene-2-Carbonyl)Guanidine Methanesulfonate The title compound was prepared as a white solid (195 mg, 0.48 mmol, 68%) in the same manner as in Example 1, with the exception that the compound (200 mg, 0.70 mmol) obtained in Preparative Example 44 was used.

$^1$H NMR(300 MHz, DMSO) δ 11.65(br s, 1H), 8.39(s, 1H), 8.27(br s, 4H), 8.05(d, 1H, J=8.1 Hz), 7.56(d, 1H, J=8.4 Hz), 2.50(s, 3H), 2.36(s, 3H)

MS(m/z)M$^+$=313 (M$^+$)

EXAMPLE 46

Preparation of (4-Chloro-5-Methylbenzothiophene-2-Carbonyl)Guanidine Methanesulfonate The title compound was prepared as a white solid (260 mg, 0.71 mmol, 86%) in the same manner as in Example 1, with the exception that the compound (200 mg, 0.83 mmol) obtained in Preparative Example 45 was used.

$^1$H NMR(300 MHz, CD$_3$OD) δ 8.40(s, 1H), 7.85(d, 1H, J=8.3 Hz), 7.51(d, 1H, J=8.3 Hz), 2.73(s, 3H), 2.54(s, 3H)

MS(m/z)M$^+$=267 (M$^+$)

EXAMPLE 47

Preparation of
(4,5-Dimethylbenzothiophene-2-Carbonyl)Guanidine
Methanesulfonate The title compound was prepared as a white solid (98 mg, 0.29 mmol, 70%) in the same manner as in Example 1, with the exception that the compound (90 mg, 0.41 mmol) obtained in Preparative Example 46 was used.

$^1$H NMR(300 MHz, CD$_3$OD) δ 8.62 (s, 1H), 7.92(d, 1H, J=8.2 Hz), 7.59(d, 1H, J=8.3 Hz), 2.94(s, 3H), 2.84(s, 3H), 2.65(s, 3H)

MS (m/z)M$^+$=247 (M$^+$)

EXAMPLE 48

Preparation of (4-Cyano-5-Methylbenzothiophene-2-Carbonyl)Guanidine Methanesulfonate The title compound was prepared as a white solid (78 mg, 0.22 mmol, 64%) in the same manner as in Example 1, with the exception that the compound (80 mg, 0.35 mmol) obtained in Preparative Example 47 was used.

$^1$H NMR(300 MHz, CD$_3$OD) δ 8.36(s, 1H), 8.21(d, 1H, J=8.4 Hz), 7.61(d, 1H, J=8.4 Hz), 2.72(s, 3H), 2.71(s, 3H)

MS(m/z)M$^+$=258 (M$^+$)

EXAMPLE 49

Preparation of (4-Bromo-6-Methylbenzothiophene-2-Carbonyl)Guanidine Methanesulfonate The title compound was prepared as a white solid (108 mg, 0.27 mmol, 75%) in the same manner as in Example 1, with the exception that the compound (100 mg, 0.35 mmol) obtained in Preparative Example 48 was used.

$^1$H NMR(300 MHz, CD$_3$OD) δ 8.48(s, 1H), 7.97(s, 1H), 7.75(s, 1H), 2.89(s, 3H), 2.67(s, 3H)

MS(m/z)M$^+$=313 (M$^+$)

EXAMPLE 50

Preparation of
(4,6-Dimethylbenzothiophene-2-Carbonyl)Guanidine
Methanesulfonate The title compound was prepared as a white solid (75 mg, 0.22 mmol, 39%) in the same manner as in Example 1, with the exception that the compound (125 mg, 0.57 mmol) obtained in Preparative Example 49 was used.

$^1$H NMR(300 MHz, CD$_3$OD) δ 8.31(s, 1H), 7.61(s, 1H), 7.15(s, 1H), 2.72(s, 3H), 2.66(s, 3H), 2.47(s, 3H)

MS(m/z)M$^+$=247 (M$^+$)

EXAMPLE 51

Preparation of (4-Cyano-6-Methylbenzothiophene-2-Carbonyl)Guanidine Methanesulfonate The title compound was prepared as a white solid (135 mg, 0.38 mmol, 80%) in the same manner as in Example 1, with the exception that the compound (110 mg, 0.48 mmol) obtained in Preparative Example 50 was used.

$^1$H NMR(300 MHz, CD$_3$OD) δ 8.38(s, 1H), 8.16(s, 1H), 7.83(s, 1H), 2.73(s, 3H), 2.57(s, 3H)

MS (m/z) M$^+$=258 (M$^+$)

The compounds of the present invention prepared in the examples are represented in Table 1 below.

TABLE 1-continued

| Ex. No. | Structure | |
|---|---|---|
| 11 | 4-(2-methoxyphenyl)-benzo[b]thiophene-2-carboxamidine | CH₃SO₃H |
| 12 | 4-(3-methoxyphenyl)-benzo[b]thiophene-2-carboxamidine | CH₃SO₃H |
| 13 | 4-(4-methoxyphenyl)-benzo[b]thiophene-2-carboxamidine | CH₃SO₃H |
| 14 | 4-(2-trifluoromethylphenyl)-benzo[b]thiophene-2-carboxamidine | CH₃SO₃H |
| 15 | 4-(3-trifluoromethylphenyl)-benzo[b]thiophene-2-carboxamidine | CH₃SO₃H |
| 16 | 4-(4-trifluoromethylphenyl)-benzo[b]thiophene-2-carboxamidine | CH₃SO₃H |
| 17 | 4-phenyl-benzo[b]thiophene-2-carboxamidine | CH₃SO₃H |
| 18 | 4-(naphthalen-1-yl)-benzo[b]thiophene-2-carboxamidine | CH₃SO₃H |
| 19 | 4-(3,5-dichlorophenyl)-benzo[b]thiophene-2-carboxamidine | CH₃SO₃H |
| 20 | 4-(2,5-dichlorophenyl)-benzo[b]thiophene-2-carboxamidine | CH₃SO₃H |
| 21 | 4-(2,3-dichlorophenyl)-benzo[b]thiophene-2-carboxamidine | CH₃SO₃H |

TABLE 1-continued

| Ex. No. | Structure | |
|---|---|---|
| 22 | 4-(5-chloro-2-methoxyphenyl)benzo[b]thiophene-2-carboxamidine | CH₃SO₃H |
| 23 | 4-(3-chloro-4-fluorophenyl)benzo[b]thiophene-2-carboxamidine | CH₃SO₃H |
| 24 | 4-(3,5-difluorophenyl)benzo[b]thiophene-2-carboxamidine | CH₃SO₃H |
| 25 | 4-(2,5-difluorophenyl)benzo[b]thiophene-2-carboxamidine | CH₃SO₃H |
| 26 | 4-(2,3-difluorophenyl)benzo[b]thiophene-2-carboxamidine | CH₃SO₃H |
| 27 | 4-(3,4-difluorophenyl)benzo[b]thiophene-2-carboxamidine | CH₃SO₃H |
| 28 | 4-(5-fluoro-2-methylphenyl)benzo[b]thiophene-2-carboxamidine | CH₃SO₃H |
| 29 | 4-(2-fluoro-5-methylphenyl)benzo[b]thiophene-2-carboxamidine | CH₃SO₃H |
| 30 | 4-(3,5-dimethylphenyl)benzo[b]thiophene-2-carboxamidine | CH₃SO₃H |
| 31 | 4-(2,5-dimethylphenyl)benzo[b]thiophene-2-carboxamidine | CH₃SO₃H |
| 32 | 4-chlorobenzo[b]thiophene-2-carboxamidine | CH₃SO₃H |
| 33 | 4-fluorobenzo[b]thiophene-2-carboxamidine | CH₃SO₃H |
| 34 | 4-iodobenzo[b]thiophene-2-carboxamidine | CH₃SO₃H |
| 35 | 4-methylbenzo[b]thiophene-2-carboxamidine | CH₃SO₃H |

TABLE 1-continued

| Ex. No. | Structure | |
|---|---|---|
| 36 | 4-vinyl-benzothiophene-2-carbonylguanidine | methanesulfonic acid |
| 37 | 4-ethyl-benzothiophene-2-carbonylguanidine | methanesulfonic acid |
| 38 | 4-isopropyl-benzothiophene-2-carbonylguanidine | methanesulfonic acid |
| 39 | 4-nitro-benzothiophene-2-carbonylguanidine | methanesulfonic acid |
| 40 | 4-amino-benzothiophene-2-carbonylguanidine | methanesulfonic acid |
| 41 | 4-methoxy-benzothiophene-2-carbonylguanidine | methanesulfonic acid |
| 42 | 4-cyano-benzothiophene-2-carbonylguanidine | methanesulfonic acid |
| 43 | 4-trifluoromethyl-benzothiophene-2-carbonylguanidine | methanesulfonic acid |
| 44 | benzothiophene-2-carbonylguanidine | methanesulfonic acid |
| 45 | 4-bromo-5-methyl-benzothiophene-2-carbonylguanidine | methanesulfonic acid |
| 46 | 4-chloro-5-methyl-benzothiophene-2-carbonylguanidine | methanesulfonic acid |
| 47 | 4,5-dimethyl-benzothiophene-2-carbonylguanidine | methanesulfonic acid |
| 48 | 4-cyano-5-methyl-benzothiophene-2-carbonylguanidine | methanesulfonic acid |
| 49 | 4-bromo-6-methyl-benzothiophene-2-carbonylguanidine | methanesulfonic acid |
| 50 | 4,6-dimethyl-benzothiophene-2-carbonylguanidine | methanesulfonic acid |
| 51 | 4-cyano-6-methyl-benzothiophene-2-carbonylguanidine | methanesulfonic acid |

Compounds of Formula 1 according to the present invention were assayed for various biochemical and pharmacologic activities through the following experiments.

EXPERIMENTAL EXAMPLE 1

Inhibitory Effect on NHE-1

The benzothiophen-2-carbonylguanidine derivatives of the present invention were examined for NHE-1 inhibitory effect in cells according to the following procedure.

Human NHE-1 was expressed in CCL39-derived PS120 cells. These human NHE-1 expressed cells were cultured in DMEM (Dulbecco's modified Eagle's medium) supplemented with 10% fetal bovine serum, 1% penicillin/streptomycin (100× solution), 1% L-glutamine (200 mM aqueous solution). The PS120/NHE-1 cells grown in 100 mm dishes were treated with trypsin at 80-90% confluency, followed by washing with PBS (phosphate buffer saline) once, and then once with an Na-free buffer (138.2 mM Choline chloride, 4.9 mM KCl, 1.5 nM $CaCl_2 \cdot 2H_2O$, 1.2 mM $MgSO_4 \cdot 7H_2O$, 1.2 mM $KH_2PO_4$, 15 mM D-glucose, 20 mM HEPES, at pH 7.4). After centrifugation, the pellet was suspended in an Na-free buffer containing 20 mM $NH_4Cl$ and 10 μM BCECF-AM [2',7'-bis(2-carboxyethyl)-5,6-carboxy-fluorescein acetoxymethyl ester] and incubated at 37° C. for 30 min in a $CO_2$ incubator. After being harvested by centrifugation, the PS120/NHE-1 cells were washed once with an Na-free buffer to remove both $NH_4Cl$ and extracellular BCECF-AM, suspended at a density of $2.5 \times 10^4$ cells/10 μl and stored at 4° C. in a dark room until reuse. In each well of 96-well microplates, 180 μl of HBS (137 mM NaCl, 4.9 mM KCl, 1.5 mM $CaCl_2 \cdot 2H_2O$, 1.2 mM $MgSO_4 \cdot 7H_2O$, 1.2 mM $KH_2PO_4$, 15 mM D-glucose, 20 mM HEPES, at pH 7.4) and 10 μl of DMSO or 10 μl of a solution of the compound (0.03~10 μM) of the present invention in DMSO were placed and well mixed, after which 10 μl aliquots of the intracellular acidosis-induced PS120/NHE-1 cells were added thereto. 4 min after the cell addition, fluorescence (excitation: 485/444 nm, emission: 535 nm) was measured in the GEMINI-XS Microplate Spectrofluorometer (Molecular Devices). The fluorescence measured was converted into pH values using a high-$K^+$/nigericin technique. The cells in which intracellular acidosis was induced with $NH_4Cl$ prepulses, were recovered to normal pH values through the operation of NHE-1. The inhibitory effect of the compound against NHE-1 was evaluated as concentrations at which the recovery from the intracellular acidosis to a normal state was 50% inhibited ($IC_{50}$ values), with cariporide used as a control.

The results were shown in Table 2, below.

TABLE 2

Inhibitory Effect of Compounds of the Invention On NHE-1

| Cpds. | $R^1$ | $R^2$ | $IC_{50}$ (μM) |
|---|---|---|---|
| Cariporide | — | — | 0.68 |
| Exmp. 1 | Br | H | 0.20 |
| Exmp. 2 | 2-Cl-Ph | H | 4.15 |
| Exmp. 3 | 3-Cl-Ph | H | 2.52 |
| Exmp. 4 | 4-Cl-Ph | H | >30 |
| Exmp. 5 | 2-F-Ph | H | 10.52 |
| Exmp. 6 | 3-F-Ph | H | 5.62 |
| Exmp. 7 | 4-F-Ph | H | 3.90 |
| Exmp. 8 | 2-Me-Ph | H | 7.66 |
| Exmp. 9 | 3-Me-Ph | H | 3.37 |
| Exmp. 10 | 4-Me-Ph | H | >30 |
| Exmp. 11 | 2-OMe-Ph | H | >30 |
| Exmp. 12 | 3-OMe-Ph | H | 10.70 |
| Exmp. 13 | 4-OMe-Ph | H | >30 |
| Exmp. 14 | 2-$CF_3$-Ph | H | >30 |
| Exmp. 15 | 3-$CF_3$-Ph | H | 4.39 |
| Exmp. 16 | 4-$CF_3$-Ph | H | >30 |
| Exmp. 17 | Ph | H | 8.36 |
| Exmp. 18 | 1-naphthalenyl | H | >30 |
| Exmp. 19 | 3,5-diCl-Ph | H | 0.68 |
| Exmp. 20 | 2,5-diCl-Ph | H | >30 |
| Exmp. 21 | 2,3-diCl-Ph | H | >30 |
| Exmp. 22 | 2-OMe-5-Cl-Ph | H | >30 |
| Exmp. 23 | 3-Cl-4-F-Ph | H | 2.48 |
| Exmp. 24 | 3,5-diF-Ph | H | 5.10 |
| Exmp. 25 | 2,5-diF-Ph | H | 8.57 |
| Exmp. 26 | 2,3-diF-Ph | H | 8.93 |
| Exmp. 27 | 3,4-diF-Ph | H | 3.62 |
| Exmp. 28 | 2-Me-5-F-Ph | H | 4.79 |
| Exmp. 29 | 2-F-5-Me-Ph | H | 6.69 |
| Exmp. 30 | 3,5-diMe-Ph | H | >30 |
| Exmp. 31 | 2,5-diMe-Ph | H | 10.09 |
| Exmp. 32 | Cl | H | 0.20 |
| Exmp. 33 | F | H | 1.73 |
| Exmp. 34 | I | H | 0.17 |
| Exmp. 35 | Me | H | 0.48 |
| Exmp. 36 | vinyl | H | 0.31 |
| Exmp. 37 | Et | H | 0.27 |
| Exmp. 38 | iPr | H | 0.85 |
| Exmp. 39 | $NO_2$ | H | 2.34 |
| Exmp. 40 | $NH_2$ | H | >30 |
| Exmp. 41 | OMe | H | 3.44 |
| Exmp. 42 | CN | H | 2.02 |
| Exmp. 43 | $CF_3$ | H | 0.40 |
| Exmp. 44 | H | | 11.70 |
| Exmp. 45 | Br | 5-Me | 0.29 |
| Exmp. 46 | Cl | 5-Me | 0.54 |
| Exmp. 47 | Me | 5-Me | 0.75 |
| Exmp. 48 | CN | 5-Me | — |
| Exmp. 49 | Br | 6-Me | — |
| Exmp. 50 | Me | 6-Me | — |
| Exmp. 51 | CN | 6-Me | — |

As shown in Table 2, the control cariporide showed a potent inhibitory effect on NHE-1, with an $IC_{50}$ value of 0.68 μM. Compounds of Examples 1, 3, 19, 23, 32~39, 41~43, and 45~47 according to the present invention inhibited NHE-1, with $IC_{50}$ values below 3.0 μM. Especially, compounds of Examples 1, 32, 34, 36, 37, 43 and 45 had $IC_{50}$ values less than 0.5 μM, showing more potent inhibition on NHE-1 than that of cariporide.

Hence, the compounds of the present invention could be used as cardioprotectives against ischemia/reperfusion injury owing to their potent inhibitory effect on NHE-1.

EXPERIMENTAL EXAMPLE 2

Cardioprotective Effect in Isolated Ischemic Rat Heart Model

For examining whether the benzothiophen-2-carbonylguanidine derivatives of the present invention were cardioprotective, the heart was excised from rats according to the Langendorff heart preparation method.

Male rats (300~450 g, the Korea Research Institute of Chemical Technology, Experimental Animal Lab) were anesthetized by intraperitoneal injection with sodium pentobarbital at a dose of 100 mg/kg and were intravenously administered with heparine at a dose of 1000 U/kg, followed by the excision of the heart. In detail, a tracheotomy was performed and a tracheal cannula (PE 240) was inserted into the trachea for subsequent artificial ventilation with room air using a rodent ventilator. Following thoracotomy, the heart was rapidly excised, mounted on a Langendorff apparatus and perfused via retrograde cannulation of the aorta at a constant perfusion pressure of 85 mmHg using a 37° C. physiological buffer saturated with 95% $O_2$/5% $CO_2$ (modified Krebs-Henseleit bicarbonate buffer; composition <mM/L>: 116 NaCl, 4.7 KCl, 1.1, MgSO4, 1.17 $KH_2PO_4$, 24.9 $NaHCO_3$, 2.52 $CaCl_2$, 8.32 Glucose, 2.0 Pyruvate).

A catheter tip manometer connected to a latex balloon filled with a mixture of ethanol and distilled water (1:1 v/v) was inserted via an incision in the left atrium into the left ventricle, and the intraventricular pressure thereof transmitted to the latex balloon was measured isovolumetrically with a transducer and recorded on a recording system (Linearcorder mark 8 WR 3500) with the aid of an amplifier (Plugsys bridge amplifier). After stabilizing the heart for 15 min, the balloon volume was adjusted to create a left ventricular end-diastolic pressure (LVEDP) of 5 mmHg during the initial baseline period. The volume of the balloon was maintained until the end of the experiment.

Baseline heart contraction function, spontaneous heart rate (HR) and coronary flow (CF) were determined from the left ventricular contraction interval. The left ventricular developed pressure (LVDP), which is regarded as an index of contractile function of the isolated heart, was calculated by subtracting left ventricular end-diastolic pressure (LVEDP) from left ventricular peak systolic pressure (LVSP). In contrast to the heart in the body, the Langendorff heart cannot be measured for cardiac output and thus, RPP (rate-pressure product), which is an important indirect indicator for cardiac performance, was calculated by multiplying heart rate (HR) by LVDP. Throughout the experiment, the temperature of the heart was maintained constant by immmersing the heart in a 37° C. physiological solution to which 95% $O_2$/5% $CO_2$ was continuously supplied. The heart thus stabilized was perfursed for 10 min with a solution of the compounds of the invention or control drugs in DMSO (dimethylsulfoxide) diluted with HBS (final DMSO conc. 0.04%), or with the solvent only (a negative control; 0.04% DMSO) and then measured again for contractile function, heart rate (HR) and coronary flow (CF). The supply of perfusates was completely stopped for 30 min in order to induce global ischemia in the heart, followed by reperfusion for 30 min. The indices (LVDP, HR, LVEDP, and CF) were measured again. After the reperfusion, the total level of lactate dehydrogenase (LDH) in the reperfusates was measured using a kit and taken as an index of ischemic myocardial injury. A negative control group was treated with the solvent only while cariporide was used as a positive control.

The results were summarized in Table 3, below.

TABLE 3

Cardioprotective Effects of the Compounds of the Invention

| Cpds. | Conc. (μM) | RPP[1] (%) | LVEDP[2] (mmHg) | LDH[3] (u/g) |
|---|---|---|---|---|
| Negative Control | — | 15.5 | 55.3 | 33.6 |
| Cariporide | 10 | 69.8 | 22.4 | 19.3 |
| Example 1 | 10 | 54.7 | 34.0 | NA[4] |
| Example 19 | 10 | 19.1 | 64.4 | NA[4] |
| Example 23 | 10 | 5.9 | 68.0 | 8.8 |
| Example 32 | 10 | 60.8 | 25.3 | 8.8 |
| Example 33 | 10 | 46.6 | 37.7 | 7.0 |
| Example 34 | 10 | 65.8 | 19.0 | 7.1 |
| Example 35 | 10 | 40.4 | 38.0 | NA[4] |
| Example 36 | 10 | 51.0 | 42.0 | 13.1 |
| Example 37 | 10 | 43.4 | 37.7 | 7.1 |
| Example 39 | 10 | 73.3 | 11.3 | 10.8 |
| Example 42 | 10 | 82.4 | 6.0 | 14.7 |
| Example 43 | 10 | 80.6 | 5.8 | 5.2 |
| Example 45 | 10 | 50.4 | 41.8 | 22.5 |
| Example 47 | 10 | 59.3 | 25.0 | 21.2 |

[1]rate-pressure product (LVDP x HR) % relative to the value before ischemia induction
[2]left ventricular end-diastolic pressure
[3]free LDH level upon reperfusion
[4]not assayed In the isolated ischemia/reperfusion rat heart experiment, as shown in Table 3, the negative control was significantly decreased in contractile function as its RPP (LVDP×HR), an index of the contractile function of the heart, was reduced to as low as 15.5% relative to that before the ischemia induction. The reperfusional LVEDP, which indicates the myocardiac contracture upon ischemia/reperfusion, serving as an index of cardioprotective activity, significantly increased from 5 mgHg to 55.3 mmHg in the negative control. The released lactate dehydrogenase (LDH) level upon reperfusion, regarded as an index of cell injury, was measured to be 33.6 u/g.

The group treated with 10 μM of cariporide considerably improved with respect to myocardiac contractile function (LVDP×HR) after the reperfusion, amounting to as large as 69.8% of that before the ischemia induction, as compared with the negative control. The LVEDP of the cariporide-treated group was 22.4 mmHg, which was significantly low relative to that of the negative control, implying that it had a protective effect on the ischemic heart. The level of LDH upon reperfusion was significantly reduced to 19.3 u/g compared with the control.

By the treatment with 10 μM of each of the compounds of Example 1, 32-39, 42, 43, 45 and 47, which showed excellent inhibitory effects on NHE-1 in the cell experiments, significant protective effects against ischemic/reperfusion heart injury were observed. In all indices including heart contracture, LVEDP, and released LDH level, the compounds of Example 32, 34, 39, 42 and 43 were similar to or better than cariporide. Especially, the compounds of Example 39, 42, and 43 represented RPPs of 73.3, 82.3, and 80.6% relative to that before ischemia induction, LVEDPs of 11.3, 6.0, and 5.8 mmHg, and LDH levels of 10.8, 14.7, and 5.2 u/g, respectively, indicating far superior cardioprotective activity against ischemia/reperfusion to that of cariporide.

Therefore, the compounds of the present invention showed excellent protective effects on ischemic hearts by effectively improving the functional recovery of ischemia/reperfusion-induced heart injury, so that they could be effectively used for the prevention and treatment of ischemic heart diseases.

EXPERIMENTAL EXAMPLE 3

Cardioprotective Effect on in vivo Ischemic Rat Heart Model

The cardioprotective effect of the benzothiophen-2-carbonylguanidine derivatives according to the present invention in in vivo ischemic hearts was judged with regard to their antischemic effects (myocardial infarction reduction) on rats as follows.

Each male rat (300~450 g, the Korea Research Institute of Chemical Technology, Experimental Animal Lab) was anesthetized by intraperitoneal injection with sodium pentobarbital at a dose of 75 mg/kg. Tracheotomy was performed and a tube was inserted into the trachea for subsequent artificial ventilation with a stroke volume of 10 ml/kg and a respiratory rate of 60 breaths/min. The femoral vein and the femoral artery were cannulated for the administration of the compounds and for the measurement of blood pressures, respectively. Meanwhile, the body temperature of the rats, an important factor to influence experimental results in the ischemic myocardial injury model, was maintained constant at 37° C. using a homeothermic blanket control unit, with a body temperature-monitoring probe inserted into the rectum. Subsequently, rats were continuously measured for mean arterial blood pressure and heart rate HR throughout the experimental time period using a Statham P23XL pressure transducer (Grass Ins., Mass., USA) and an ECG/RATE Coupler (Hugo Sachs Electronic, Germany), respectively, with all continuous changes thereof recorded by Graphtec Linearcorder WR 3310 (Hugo Sachs Electronic).

The left coronary artery was occluded according to Selye H.'s method. In detail, after the chest of each rat was partially opened by left thoracotomy, the middle finger of the left hand was pressed against the right side of the chest of the rat to thrust out the heart which was then slightly fixed with the forefinger and the thumb of the same hand. Then, immediately after the left anterior descending coronary artery (LAD) was sutured with a 5-0 silk ligature, the heart was repositioned back in the thoracic cavity with both ends of the suture positioned outside. The ends of the suture were threaded through a PE tube (PE100, 2.5 cm) and allowed to stand for 20 min for stabilization. Through the cannula inserted into the femoral vein, a vehicle or the compounds of the invention were administered and 30 min was needed for sufficient effects of the administered compounds. Cariporide was used as a control. The ends of the suture threaded through the PE tube were pulled taut with hemostatic forceps to vertically press the PE tube against the coronary artery. After occlusion for 45 min, the hemostatic forceps were removed and reperfusion was conducted for 90 min.

The coronary artery was reoccluded in the same manner as described above, followed by the intravenous injection of 2 ml of 1% Evans blue. The intravenous injection of an excess of pentobarbital killed the rats, from which the hearts were then excised. The left ventricle was removed alone from the isolated heart and transected from the cardiac apex into 5 or 6 slices. Each slice was weighed. The image of each of the heart slices was captured using a Hi-scope, a compact vision system, and analyzed for blue-stained normal areas and non-stained areas with an image analyzing program (Image Pro Plus). In each slice, the area at risk (AAR) was calculated by multiplying the ratio of the non-stained area to the total area of the slice with the weight of the slice. Sum of the individual area at risk (AAR) for each slice was divided by the total weight of the left ventricle to obtain AAR (%) according to the following mathmatical formula 1.

$$AAR(\%) = \frac{\sum AAR \text{ for each Slice}}{\text{Total Left Ventricle Weight}} \times 100 \quad < \text{Mathmatical Formula 1} >$$

Separately, the heat slices were incubated in 1%. 2,3,5-triphenyltetrazolium chloride (TTC) phosphate buffer (pH 7.4), 37° C., for 15 min and fixed in 10% formalin for 20~24 hours. In the normal area of the tissue, 2,3,5-triphenyltetrazolium chloride was reduced by the myocardial dehydrogenase in the presence of the cofactor NADH to form formazan dye, which appeared as a brick-red color. In contrast, infarction areas of the tissue did not appear red because 2,3,5-triphenyltetrazolium chloride was not reduced due to their lack of the dehydrogenase and the cofactor.

Taking advantage of 2,3,5-triphenyltetrazolium chloride, each slice was analyzed to determine normal area and infarct size (IS) in the same manner as in AAR. The sum of the individual infarct sizes for each slice was divided by the total weight of AAR or left ventricle to calculate IS (%) according to the following Mathematical Formula 2. In this experimental model, lower IS (%) reflected smaller infarct sizes, implying more potent anti-ischemic effects of the compounds.

$$IS(\%) = \frac{\sum \text{Infarct Size for each Slice}}{\text{Total Weight of AAR or Left Ventricle}} \times 100 \quad < \text{Mathematical Formula 2} >$$

The results were shown in Table 4.

TABLE 4

| Cardioprotective Effects (in vivo) | | |
|---|---|---|
| Cpds. | | Myocardiac infarction rate (IS/AAR[1], %) |
| Negative Control | | 58.6 |
| Cariporide | 0.1 mg/kg | 40.5 |
| | 0.3 mg/kg | 37.9 |
| Example 1 | 0.1 mg/kg | 45.6 |
| Example 32 | 0.1 mg/kg | 48.1 |
| Example 33 | 0.1 mg/kg | 45.2 |
| Example 34 | 0.1 mg/kg | 48.6 |
| Example 35 | 0.1 mg/kg | 47.9 |
| Example 37 | 0.1 mg/kg | 51.6 |
| Example 42 | 0.1 mg/kg | 36.9 |
| | 0.3 mg/kg | 34.4 |
| Example 43 | 0.1 mg/kg | 44.8 |

[1]IS/AAR (infarct size/area at risk)

As is apparent from the data of Table 4, the compounds of the present invention was found to significantly reduce myocardiac infarction rates with regard to area at risk in the in-vivo ischemic myocardiac injury model.

In more detail, the vehicle-administered group had a myocardiac infarction rate relative to area at risk (IS/AAR, %) of as high as 58.6%, suffering from serious myocardiac injury. The positive control cariporide showed significant anti-ischemic activity, as it allowed myocardiac infarction rates to be 40.5% at an injection dose of 0.1 mg/kg and 37.9% at an injection dose of 0.3 mg/Kg.

When compounds of Example 1, 32, 33, 34, 35, 47 and 48 were injected at a dose of 0.1 mg/Kg each, myocardiac infarction rates less than 50% were observed, which were significantly lower than that of the negative control. Particularly, the compound of Example 42, which was evaluated to have excellent inhibitory activity against NHE-1 and highly improve the functional recovery of the isolated ischemic/reperfusional rat heart model, allowed the myocardiac infarction rate to be 36.9% at a dose of 0.1 mg/kg and 34.4% at a dose of 0.3 mg/Kg, demonstrating that it is far superior in terms of cardioprotective activity against ischemia to cariporide.

Therefore, the compounds of the present invention, as demonstrated by the low myocardiac infarction rates in in vivo ischemic heart models, effectively protected the heart from ischemia so that they could be useful for the prevention and treatment of ischemic heart disease such as myocardiac infarction, arrhythmia, angina pectoris, and the like, and are effective as cardioprotective agents for cardiac surgery, such as coronary artery bypass and percutaneous transluminal coronary angioplasty immediately.

EXPERIMENTAL EXAMPLE 4

Neuroprotective Effect

In order to examine whether the benzothiophen-2-carbonylguanidine derivatives of the present invention inhibit the neuronal cell injury and necrosis induced by glutamate, an experiment was conducted as follows.

Cortical neurons were isolated from the brain of 14-day-old fetal rats and cultured in Eagle's MEM (Minimum essential medium) at 37° C. in a 5% $CO_2$ atmosphere. On day 3 or 4 of culturing, 10 μM cytosine-β-arabinofuranoside (AraC) was added to the culture medium to prevent the overgrowth of glial cells. 80% or more of the cells grown in the medium were found to be neurons, as demonstrated by staining with NeuN (neuronal nuclei, specific neuronal markers) and GFAP (glial fibrillary acidic protein, glial cell markers). On day 7~9 of culturing, the cells were induced to cellular toxicity by treatment with 100 μM glutamate in combination with the compounds of interest or vehicle alone as a negative control. Necrosis was determined by released LDH (Lactate dehydrogenase) levels at 20 hours after glutamate treatment. For the analysis of apoptosis, the count of TUNEL (Terminal deoxynucleotidyl transferase UTP nick end labeling)-positive cells was measured at 12 hours after glutamate treatment.

The results were summarized in Table 5, below.

TABLE 5

Neuroprotective Activity Against Glutamate-Induced Neurotoxicity

| Compounds | | Free LDH Levels (necrosis) | TUNEL-Positive Cells (apoptosis) |
|---|---|---|---|
| Control | | 19.3 | 12.5 |
| Glutamate | | 58.7 | 33.3 |
| Example 42 + | 0.1 μM | 58.6 | 28.6 |
| Glutamate | 1.0 μM | 43.2 | 23.9 |
| | 10 μM | 38.8 | 18.8 |
| | 100 μM | 32.3 | 12.6 |

As seen in Table 5, the compound of Example 42 inhibited the necrosis and apoptosis of neurons in dose-dependent manners, showing neuroprotective activity against glutamate-induced neurotoxicity.

Therefore, the compounds of the present invention were highly neuroprotective, so that they could be effectively used as neuroprotective agents for cerebral ischemic diseases such as neuronal cell injury or necrosis-induced stroke or trauma.

EXPERIMENTAL EXAMPLE 5

Cerebroprotective Effect on in vivo Ischemic Rat Brain Model

In order to examine whether the benzothiophen-2-carbonylguanidine derivatives of the present invention protect the brain from ischemia-reperfusion-induced cerebral injury, the following experiment was conducted.

Male Sparague-Dawley Rats (350±50 g, Samyook Experimental Animal Lab) were anesthetized and intraperitoneally injected with heparine. After ischemia by the occlusion of the right carotid artery for 60 min, reperfusion was performed for 24 hours. Compounds or a vehicle was intravenously injected at 20 min before the occlusion.

After the perfusion for 24 hours, rats were anesthetized with a fatal dose of sodium pentobarbital. The brains were carefully isolated and transected at intervals of 2 mm. The coronary slices thus obtained were stained at 37° C. for 20 min using a 2% 2,3,5-triphenyltetrazolium chloride solution. Stained slices were analyzed for % necrosis area relative to total brain area using an image analyzer (BAS image 1500). Also, the cerebroprotective activity of the compounds against brain edema was expressed as % volume of the left hemisphere relative to that of the ischemic right hemisphere.

The results were summarized in Table 6, below.

TABLE 6

Cerebroprotective Effects Against Ischemic/Reperfusional Cerebral Injury

| Compounds | | % Infarct size/ hemisphere) | TUNEL-Positive Cells (% Right/Left Hemisphere) |
|---|---|---|---|
| Negative Control | | 25.2 | 117.04 |
| Example | 0.1 mg/kg | 21.4 | 111.2 |
| 42 | 0.3 mg/kg | 18.6 | 107.96 |

As seen in Table 6, the compound of Example 42 significantly reduced not only ischemia/reperfusion-induced brain infarction, but also brain edema at injection doses of both 0.1 mg/kg and 0.3 mg/kg.

Having superior cerebroprotective activity against ischemia/reperfusion-induced brain injury, therefore, the compounds of the present invention could be effectively used for the treatment of various diseases caused by ischemic brain injury, such as cerebral stroke.

EXPERIMENTAL EXAMPLE 6

Experiment for Acute Oral Toxicity in Rat

The benzothiophen-2-carbonylguanidine derivatives of the present invention were assayed for acute oral toxicity as follows.

Specific pathogen free (SPF) SD rats 6 weeks old were used for this experiment. Each of the compounds of Examples 1 to 51 was suspended in a 0.5% methylcellulose solution, and the suspensions were orally administered at a dose of 10 mg/kg·ml to respective groups of two rats.

After the oral administration, the rats were observed for death, clinical symptoms, change in body weight, and the like, and subjected to hematological and serobiochemical tests. Autopsy was performed to examine the abnormality of thoracic and abdominal organs with the naked eyes.

Neither particular clinical symptoms nor perished animals were observed. In addition, no acute toxicity was observed in body weight change, haematological test, serobiochemical test, and autopsy examination. These results demonstrated that the compounds tested did not induce toxicity to the dose of 10 mg/kg in rats, and were proven safe with an $LD_{50}$ of 100 mg/kg or more upon oral administration. Furthermore, the compounds according to the present invention may be formulated in various forms according to the intended purpose. Formulations containing the compounds of the present invention as effective ingredients are illustrated in the following examples, but are not construed to limit the scope of the invention.

FORMULATION EXAMPLE 1

Tablet (Direct Compression)

After being sieved, 5.0 mg of a compound of the present invention was mixed with 14.1 mg of lactose, 0.8 mg of crospovidone USUF and 0.1 mg of magnesium stearate and compressed into tablet form.

FORMULATION EXAMPLE 2

Tablet (Wetting Formula)

After being sieved, 5.0 mg of a compound of the present invention was mixed with 16.0 mg of lactose and 4.0 mg of starch. To a solution of 0.3 mg of polysolvate 80 in purified water, the mixture was added. After section to a fine size, the fine powder was dried, sieved, and mixed with 2.7 mg of colloidal silicon dioxide and 2.0 mg of magnesium stearate. Compression of the mixture gave a tablet.

FORMULATION EXAMPLE 3

Powder and Capsule 5.0 mg of a compound of the present invention was sieved and mixed with 14.8 mg of lactose, 10.0 mg of polyvinyl pyrrolidone, and 0.2 mg of magnesium stearate. The mixture was filled in a hard gelatine capsule No. 5, using a suitable apparatus.

FORMULATION EXAMPLE 4

Injection

An injection was prepared from 100 mg of a compound of the present invention, 180 mg of mannitol, mg, 26 mg of $Na_2HPO_4.12H_2O$ and 2974 mg of distilled water.

[Industrial Applicability]

As described hereinbefore, the benzothiophen-2-carbonylguanidine derivatives of the present invention are found to have potent inhibitory effect on the sodium/hydrogen exchanger NHE-1, improve the functional recovery of ischemia/reperfusion-induced heart injury in isolated ischemic heart models, and significantly reduce the myocardiac infarct size in in vivo ischemic animal models, thereby showing excellent cardioprotective effects. In addition, the compounds are protective of both neuronal cells and the brain, as proven by their protective effects on neuronal cells from necrosis and apoptosis and by their ability to significantly reduce cerebral infarct sizes in in vivo ischemic brain models.

Consequently, the pharmaceutical compositions of the present invention as well as the compounds can be effectively used for the prevention and treatment of ischemic heart diseases such as myocardiac infarction, arrhythmia, angina pectoris and the like, and cerebrovascular diseases such as cerebral stroke and the like, and be used as cardioprotective agents to the patients undergoing reperfusion therapy including chemicals such as thrombolytic agents, or surgery such as coronary artery bypass and percutaneous transluminal coronary angioplasty.

The invention claimed is:

1. A benzothiophen-2-carbonylguanidine derivative, represented by the following Formula 1, or a pharmaceutically acceptable salt thereof:

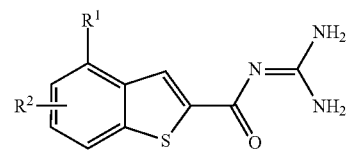

<Formula 1> wherein,
$R^1$ is CN, and
$R^2$ is H.

2. A method of preparing a benzothiophen-2-carbonylguanidine derivative or a pharmaceutically acceptable salt thereof of claim 1, in which a carboxylic acid derivative (II) is reacted with an excess of guanidine or with guanidine in the presence of a base to afford a compound (I), as represented by the following Scheme 1:

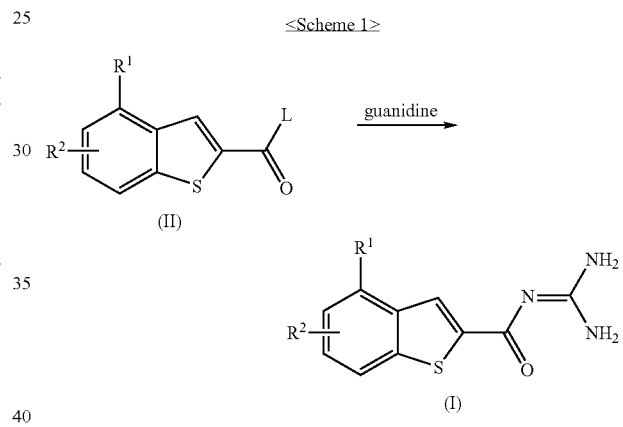

<Scheme 1> wherein, $R^1$ and $R^2$ are independently as defined in Formula 1 of claim 1, and L is a leaving group readily substitutable with guanidine.

3. A method according to claim 2, wherein the L is selected from among halogen, hydroxyl, alkoxy, mesylate and tosylate.

4. A pharmaceutical composition for the treatment of ischemic heart diseases or ischemic cerebral diseases, containing the benzothiophen-2-carbonylguanidine derivative or the pharmaceutically acceptable salt of claim 1 as an active ingredient.

* * * * *